(12) United States Patent
Cucin

(10) Patent No.: US 6,394,973 B1
(45) Date of Patent: *May 28, 2002

(54) POWER-ASSISTED LIPOSUCTION INSTRUMENT WITH CAUTERIZING CANNULA ASSEMBLY

(76) Inventor: Robert L. Cucin, 120 Central Park S., New York, NY (US) 10019

( * ) Notice: Subject to any disclaimer, the term of this patent is extended or adjusted under 35 U.S.C. 154(b) by 0 days.

This patent is subject to a terminal disclaimer.

(21) Appl. No.: 09/507,266

(22) Filed: Feb. 18, 2000

Related U.S. Application Data

(63) Continuation-in-part of application No. 08/882,927, filed on Jun. 26, 1997, now Pat. No. 5,795,323, which is a continuation of application No. 08/307,000, filed on Sep. 16, 1994, now Pat. No. 5,643,198, which is a continuation of application No. 07/627,240, filed on Dec. 14, 1990, now Pat. No. 5,348,535.

(51) Int. Cl.[7] ............................................. A61B 17/20
(52) U.S. Cl. ........................... 604/22; 604/35; 604/902; 606/50
(58) Field of Search .............................. 604/22, 35, 119, 604/268, 902; 606/167, 170, 171, 177, 50

(56) References Cited

U.S. PATENT DOCUMENTS

| | | |
|---|---|---|
| 3,082,805 A | 3/1963 | Royce |
| 3,732,858 A | 5/1973 | Banko |
| 3,734,099 A | 5/1973 | Bender et al. |
| 3,945,375 A | 3/1976 | Banko |

(List continued on next page.)

FOREIGN PATENT DOCUMENTS

| | | |
|---|---|---|
| EP | 0 125 070 A2 | 11/1984 |
| FR | 2 648 050 | 12/1990 |

OTHER PUBLICATIONS

Body Contouring with Suction Lipectomy by Kesselring, Clinics in Plastics Surgery, vol. 11, No. 3, 1984.

Illouz's Technique of Body Contouring by Lipolysis by Illouz, Clinics in Plastic Surgery, vol. 11, No. 3, 1984.

European Search Report, 1995.

*Primary Examiner*—Glenn K. Dawson
*Assistant Examiner*—Jennifer Maynard
(74) *Attorney, Agent, or Firm*—Thomas J. Perkowski, Esq., P.C.

(57) ABSTRACT

A method and apparatus is disclosed for mechanically-assisted liposuction treatment. The apparatus includes a hand-holdable housing, an electro-cauterizing cannula assembly, and a reciprocation mechanism. The hand-holdable housing has a cavity adaptable for receipt of a portion of the electro-cauterizing cannula assembly. The electro-cauterizing cannula assembly has a distal end and a proximal end and at least one aspiration aperture about the distal end. The reciprocation mechanism is disposed within the housing and is operably associated with either the cannula so that the cannulas can be selectively caused to reciprocate relative to the housing. As the cannula is caused to reciprocate relative to the housing, the aspiration aperture formed through the distal end of the cannula assembly is caused to undergo periodic displacement. During aspiration of tissue, high-voltage RF power signal supplied to an electro-cauterizing electrode structure formed about each reciprocating aspiration aperture to effect hemostasis thereabout. Such hemostasis is achieved by causing protein molecules within aspirated tissue to coagulate in response to the high-voltage RF signal being supplied across the electro-cauterizing electrode. In the preferred embodiments, the amount and rate of such aspiration aperture displacement is controllably adjustable. The cannula assembly is releasably detachable from the hand-holdable housing to facilitate cleaning and sterilization of the cannula assembly and the housing.

12 Claims, 23 Drawing Sheets

U.S. PATENT DOCUMENTS

| | | |
|---|---|---|
| 3,955,579 A | 5/1976 | Bridgman |
| 3,994,297 A | 11/1976 | Kopf |
| 4,167,944 A | 9/1979 | Banko |
| 4,203,444 A | 5/1980 | Bonnell et al. |
| 4,311,140 A | 1/1982 | Bridgman |
| 4,314,560 A | 2/1982 | Helfgott et al. |
| 4,487,600 A | 12/1984 | Brownville et al. |
| 4,530,356 A | 7/1985 | Helfgott et al. |
| 4,536,180 A | 8/1985 | Johnson |
| 4,577,629 A | 3/1986 | Martinez |
| 4,589,414 A | 5/1986 | Yoshida et al. |
| 4,735,605 A | 4/1988 | Swartz |
| 4,775,365 A | 10/1988 | Swartz |
| 4,792,327 A | 12/1988 | Swartz |
| 4,815,462 A | 3/1989 | Clark |
| 4,850,354 A | 7/1989 | McGurk-Burleson et al. |
| 4,886,491 A | 12/1989 | Parisi et al. |
| 4,909,249 A | 3/1990 | Akkas et al. |
| 4,932,935 A | 6/1990 | Swartz |
| 4,940,468 A | 7/1990 | Petillo |
| 5,024,652 A | 6/1991 | Dumenek et al. |
| 5,106,364 A | 4/1992 | Hayafuji et al. |
| 5,186,714 A | 2/1993 | Boudreault et al. |
| 5,236,414 A | 8/1993 | Takasu |
| 5,277,696 A | 1/1994 | Hagen |
| 5,290,282 A | 3/1994 | Casscells |
| 5,295,955 A * | 3/1994 | Rosen et al. .................. 604/22 |
| 5,352,194 A * | 10/1994 | Greco et al. .................. 604/35 |
| 5,364,395 A | 11/1994 | West, Jr. |
| 5,520,685 A | 5/1996 | Wojciechowicz |
| 5,643,198 A | 7/1997 | Cucin |
| 5,795,323 A * | 8/1998 | Cucin ........................ 604/22 |
| 5,797,907 A | 8/1998 | Clement |
| 6,102,885 A * | 8/2000 | Bass ......................... 604/22 |

\* cited by examiner

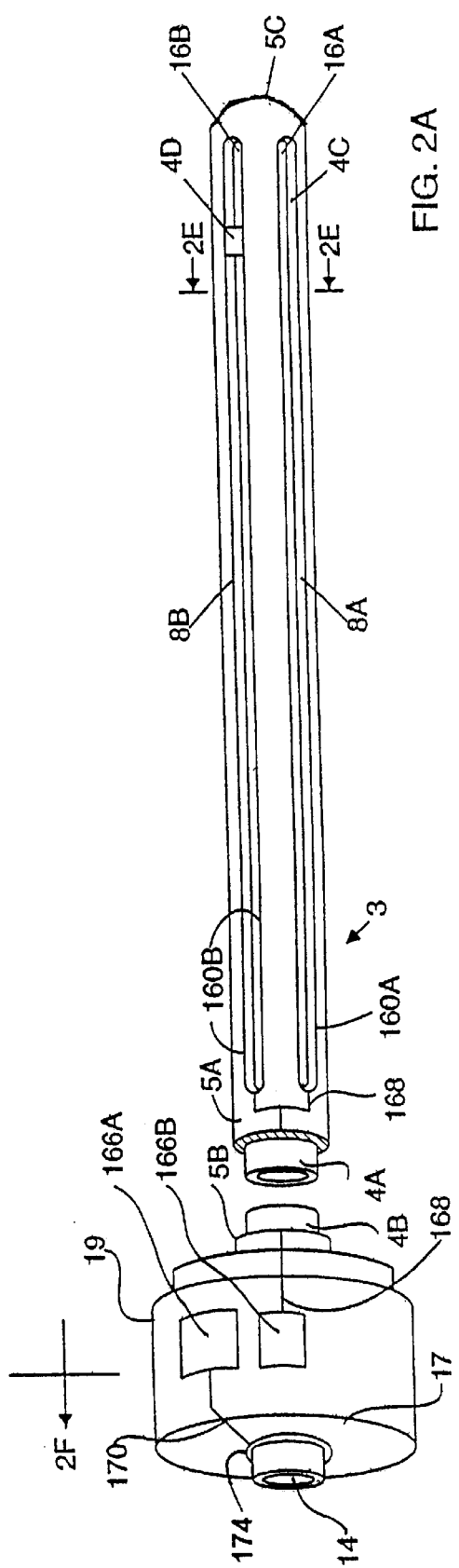
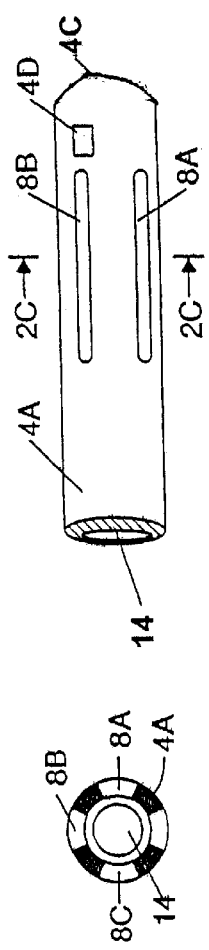
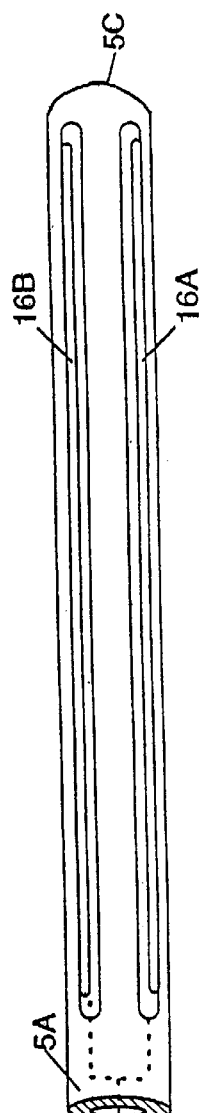
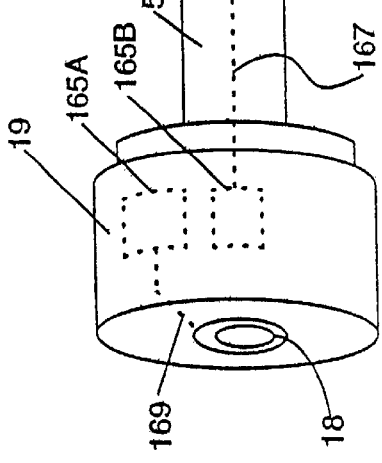
FIG. 2A
FIG. 2B
FIG. 2C
FIG. 2D

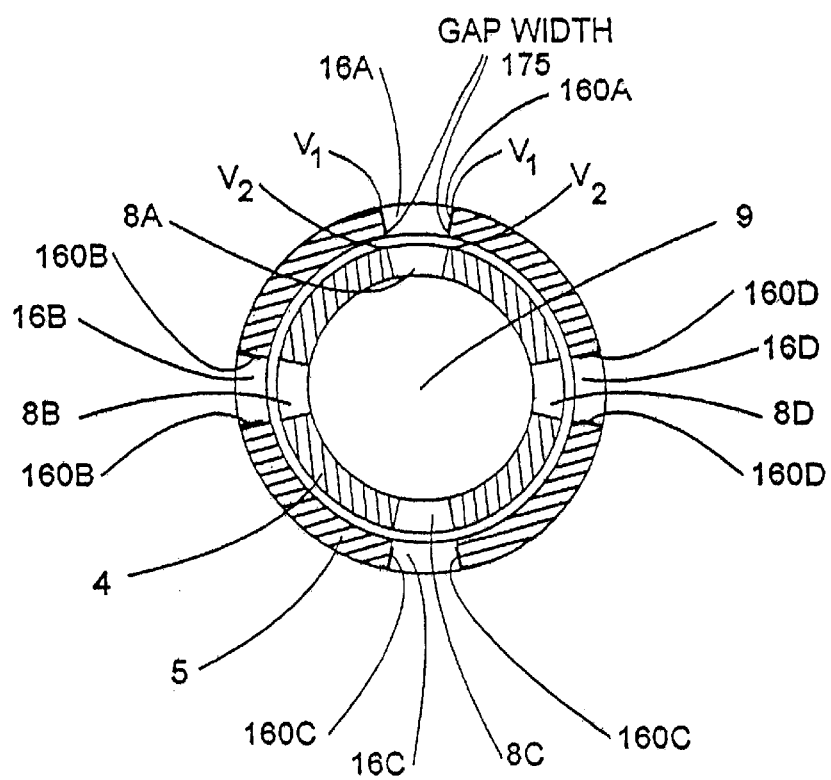
FIG. 2E
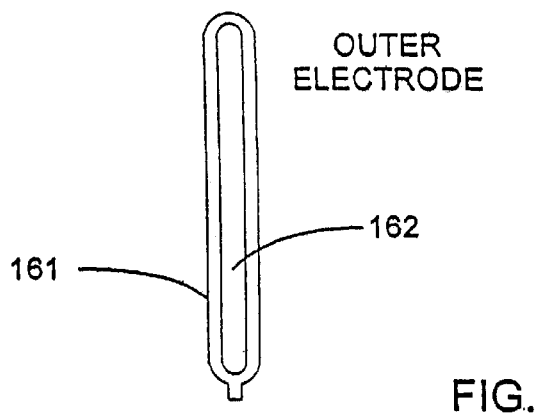
FIG. 3A
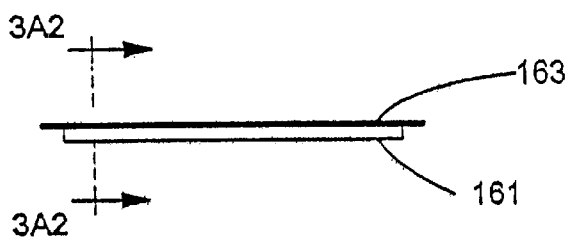
FIG. 3A1
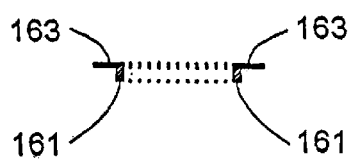
FIG. 3A2

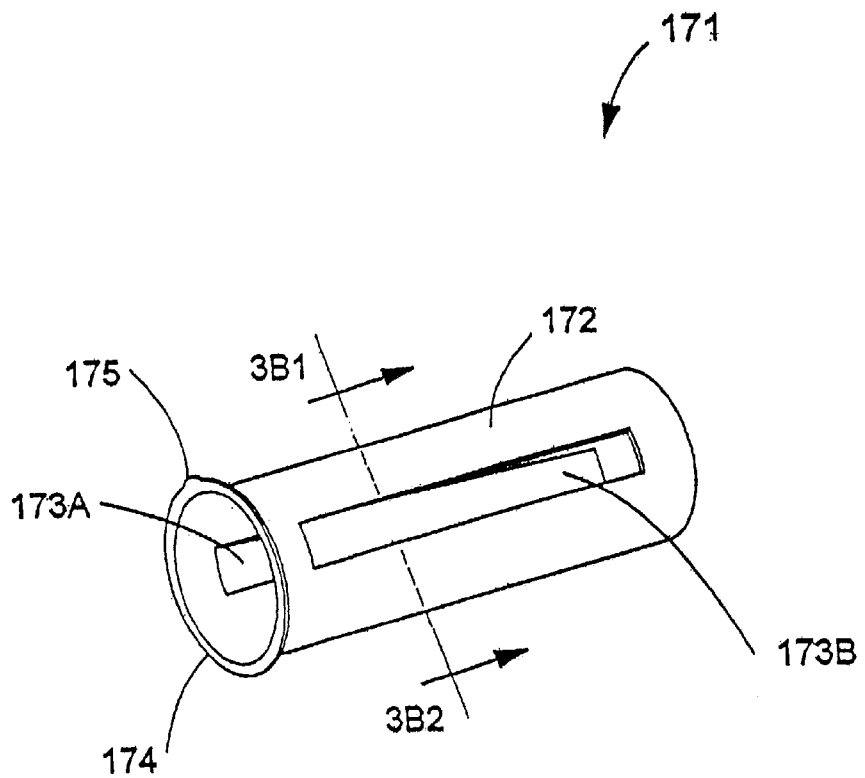
FIG. 3B
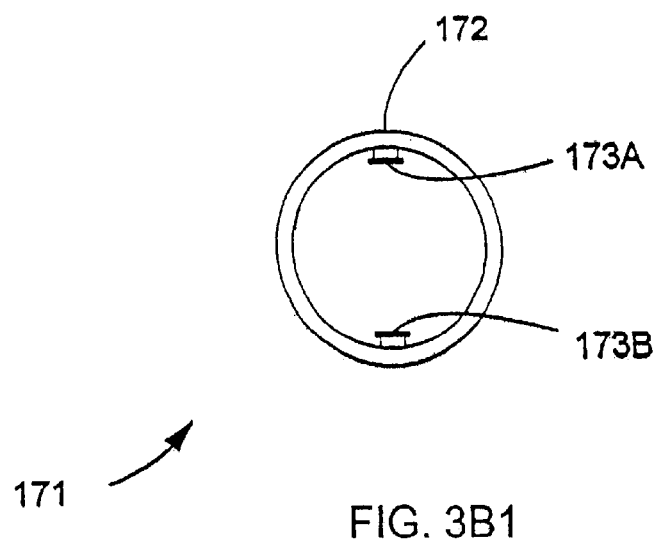
FIG. 3B1

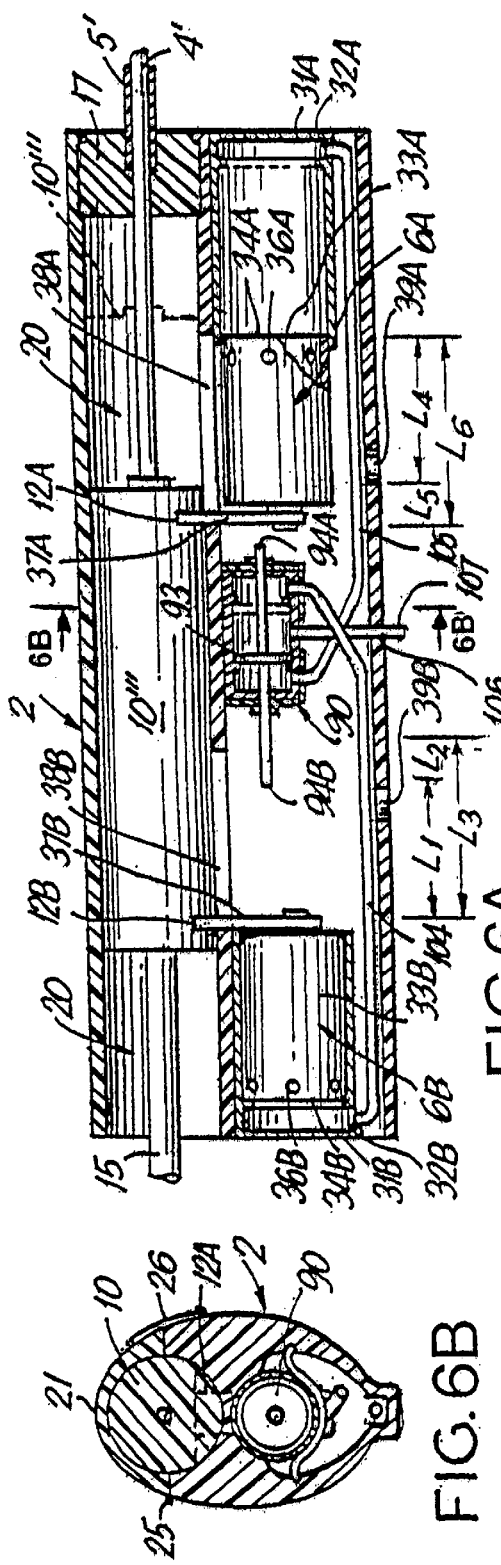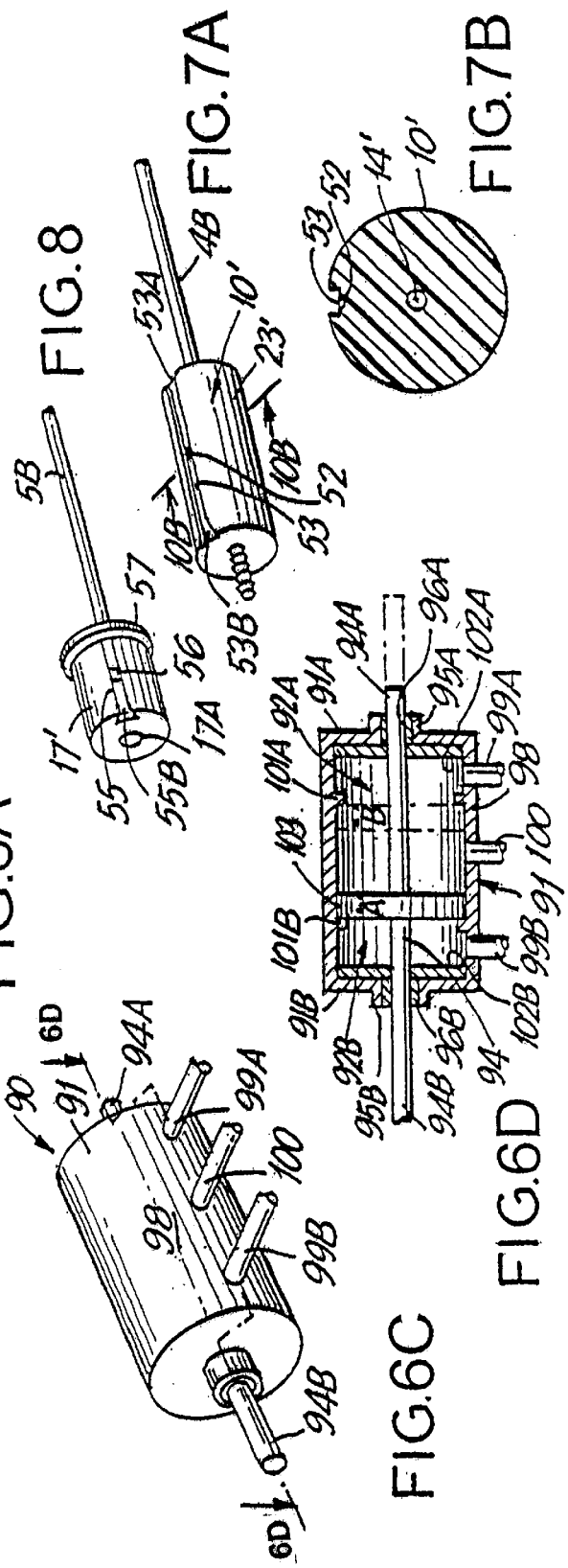

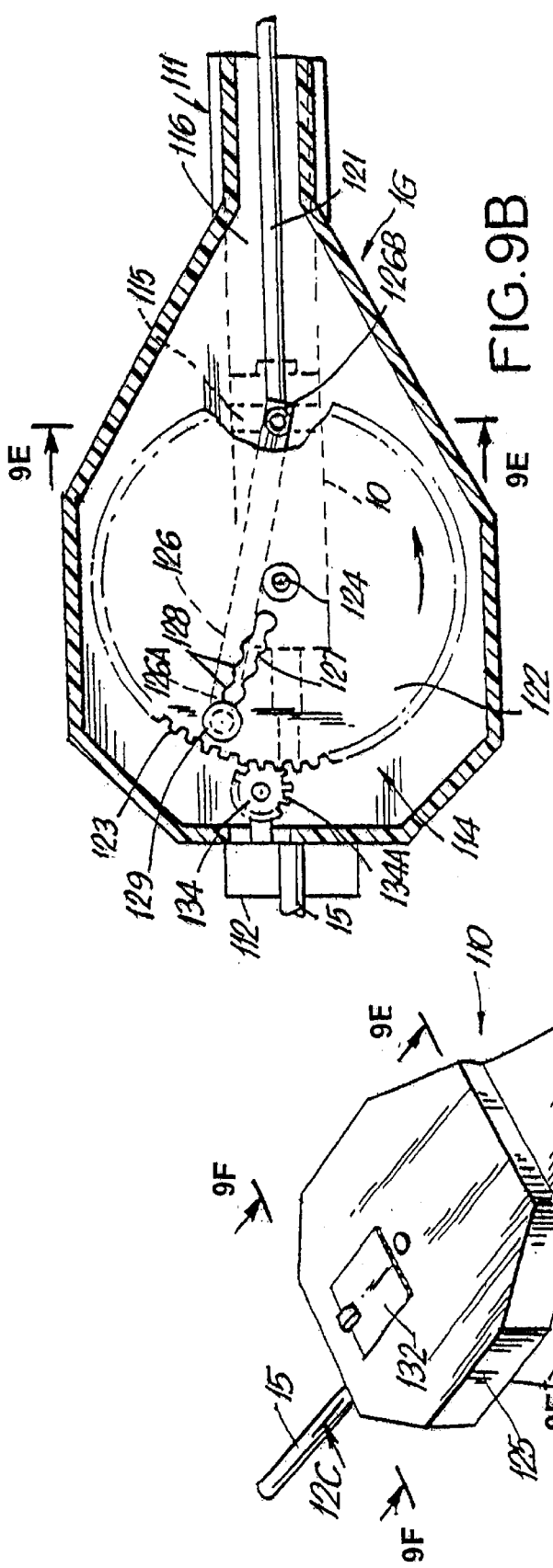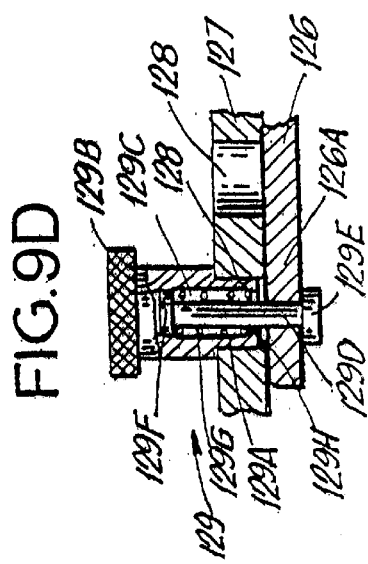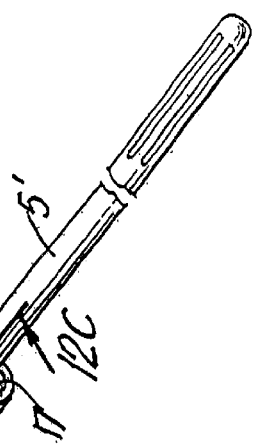

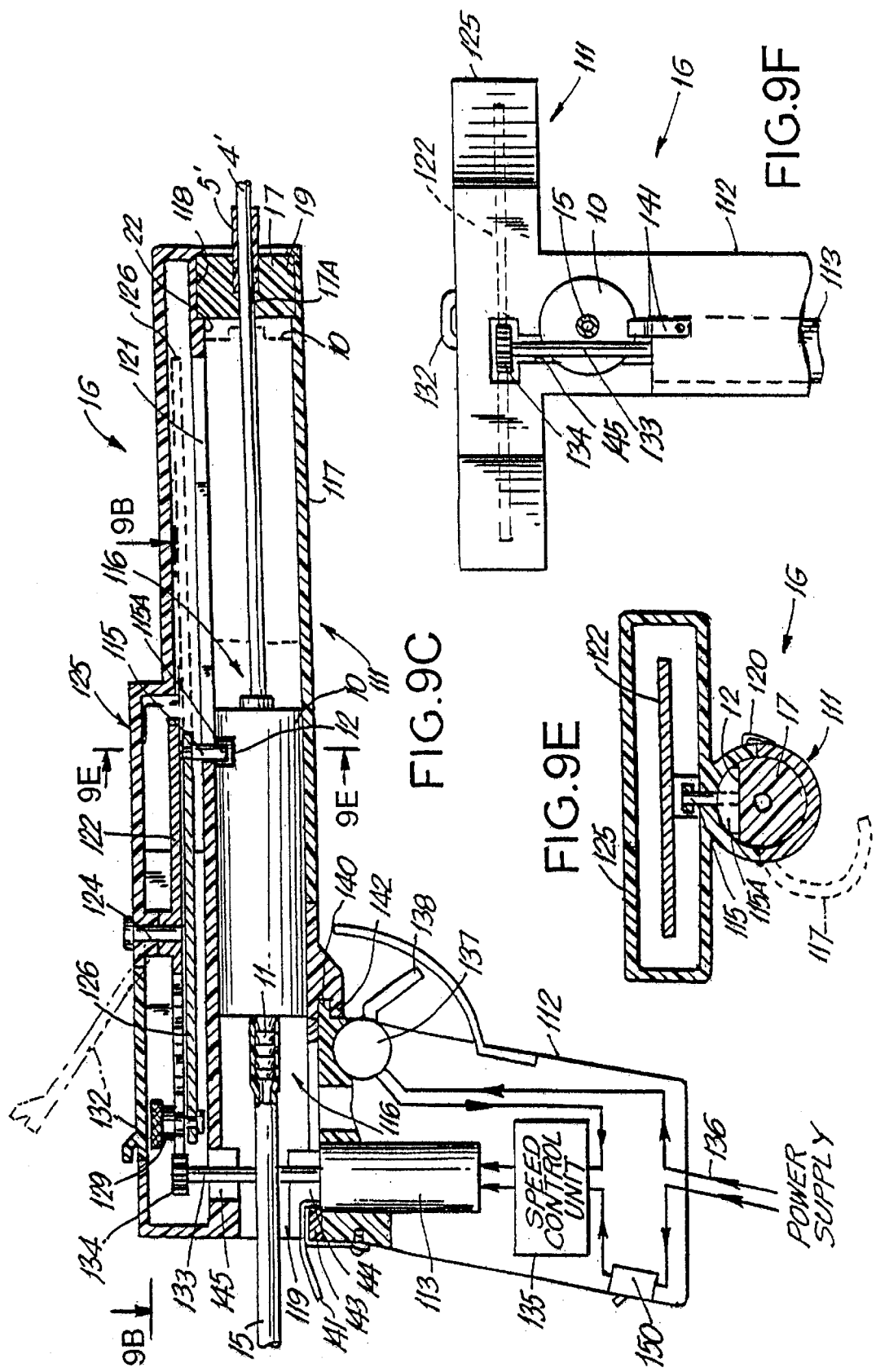

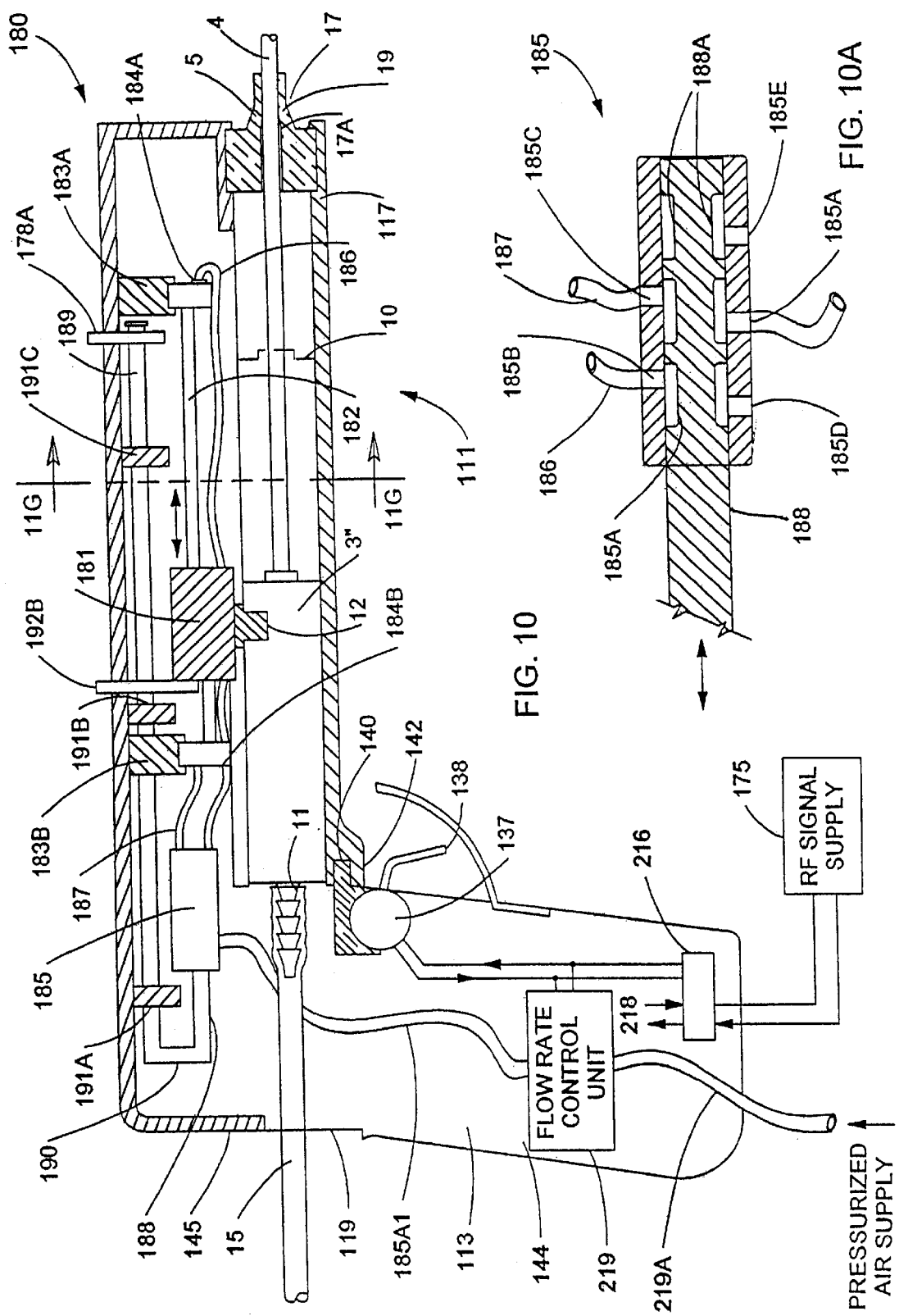

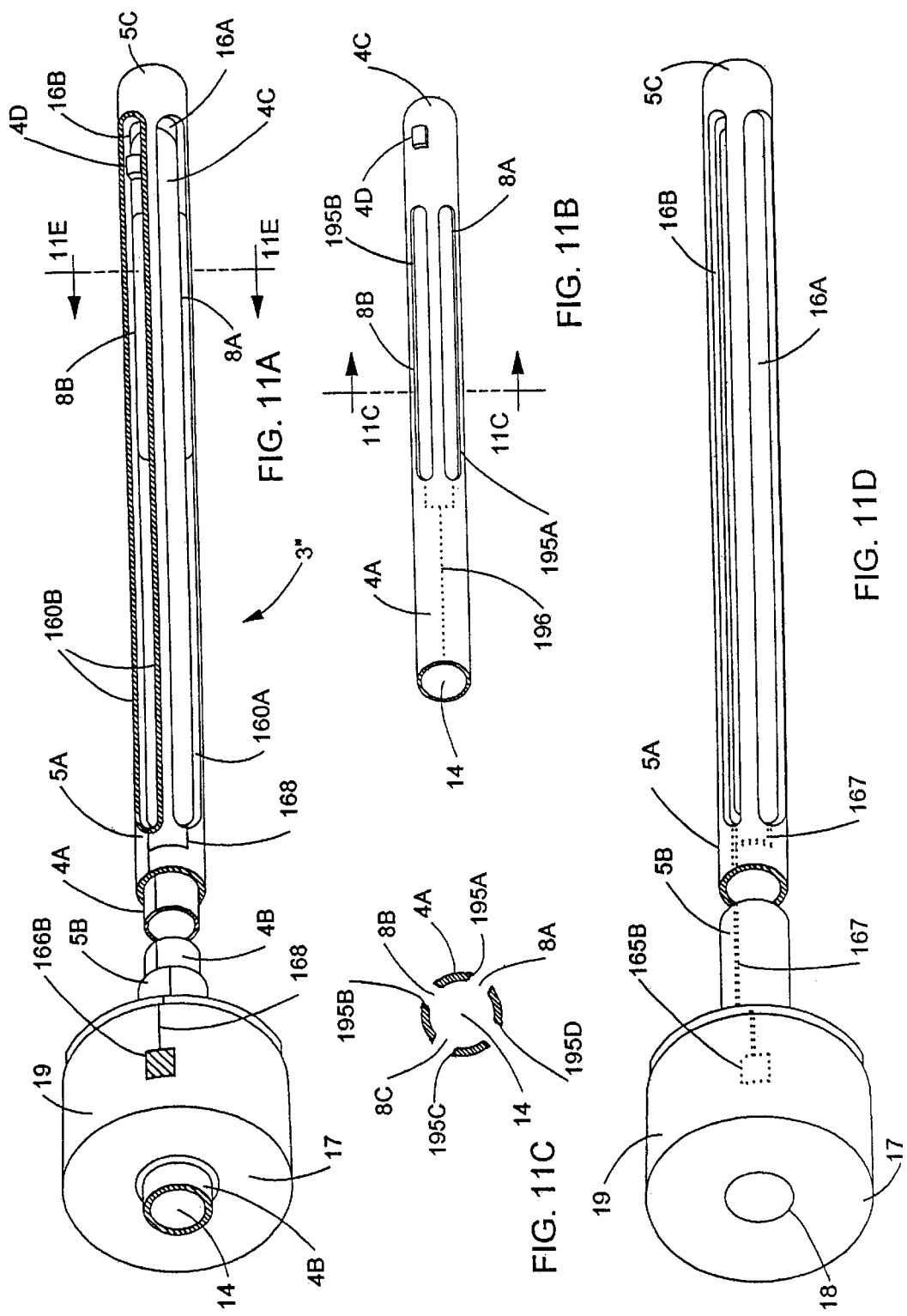

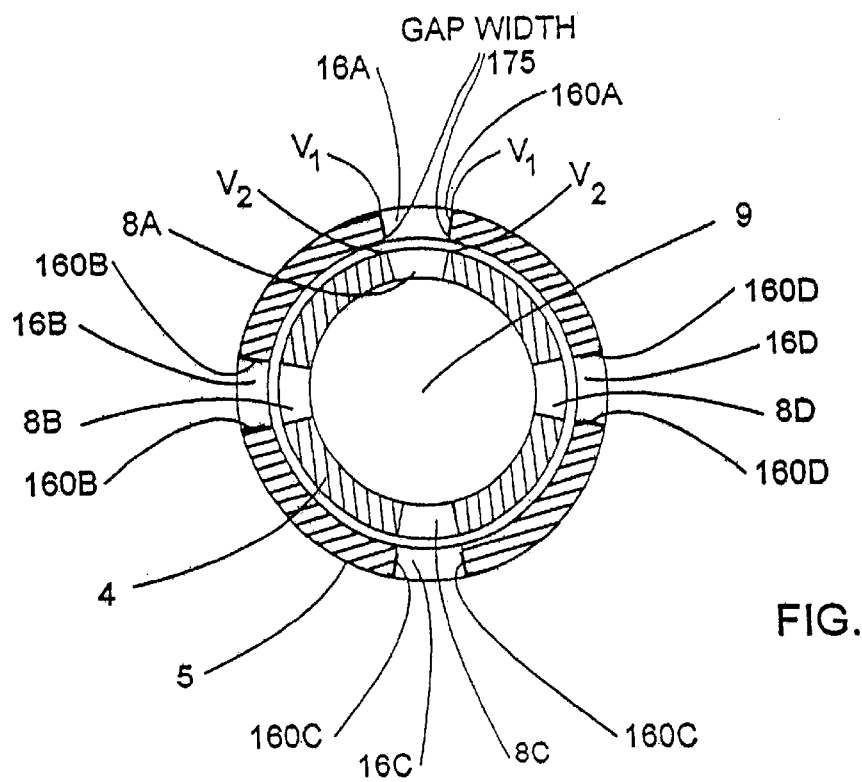
FIG. 11E
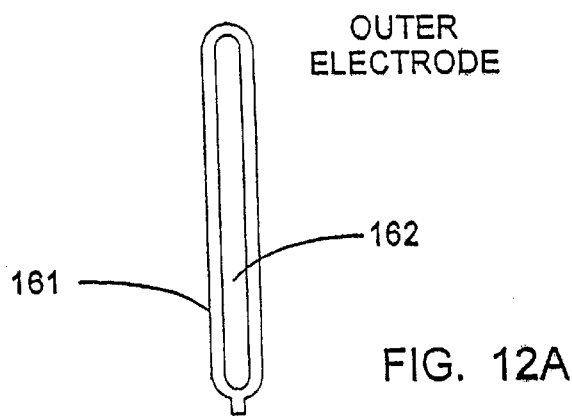
FIG. 12A
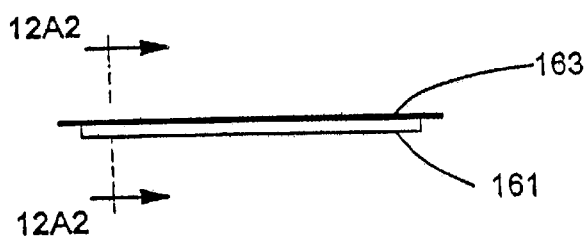
FIG. 12A1
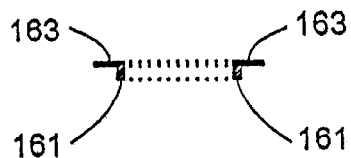
FIG. 12A2

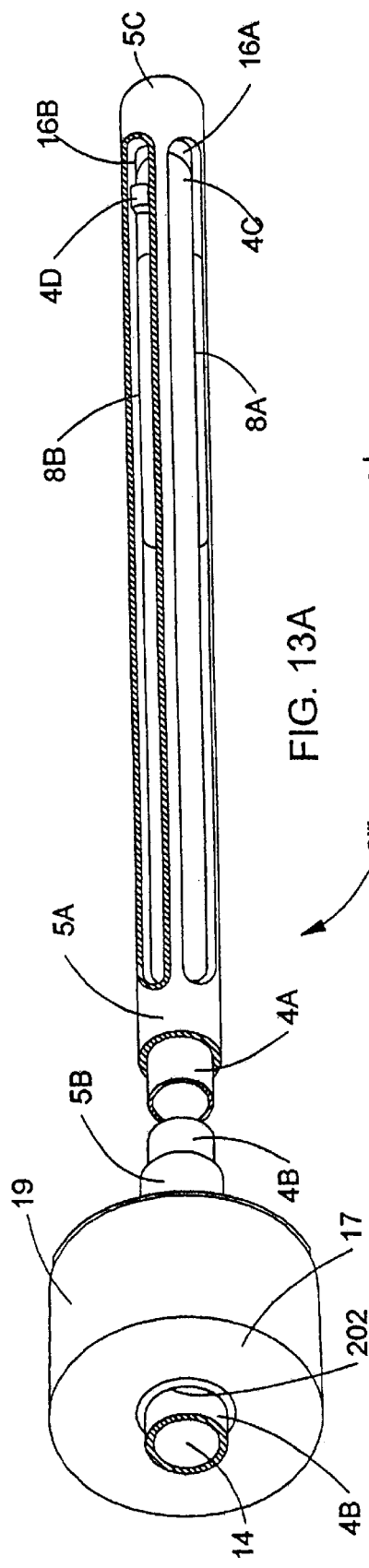
FIG. 13A
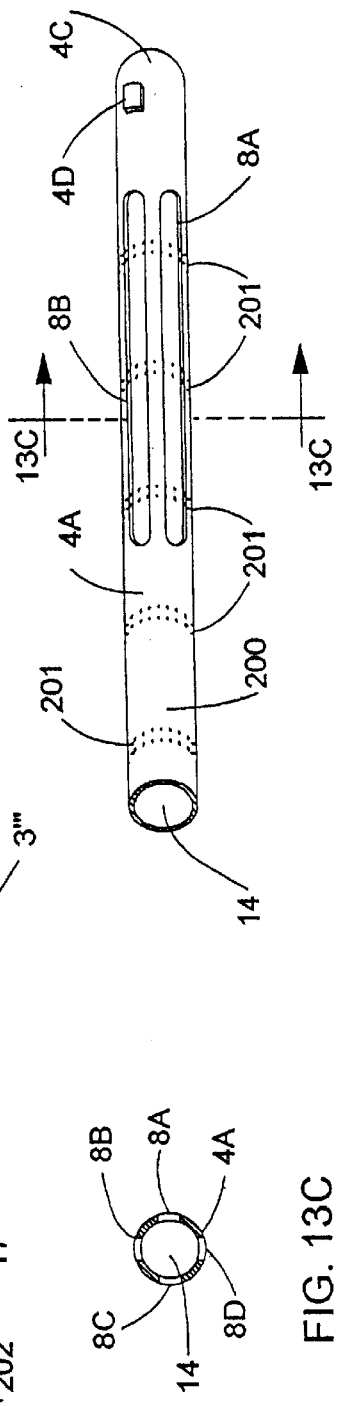
FIG. 13B
FIG. 13C
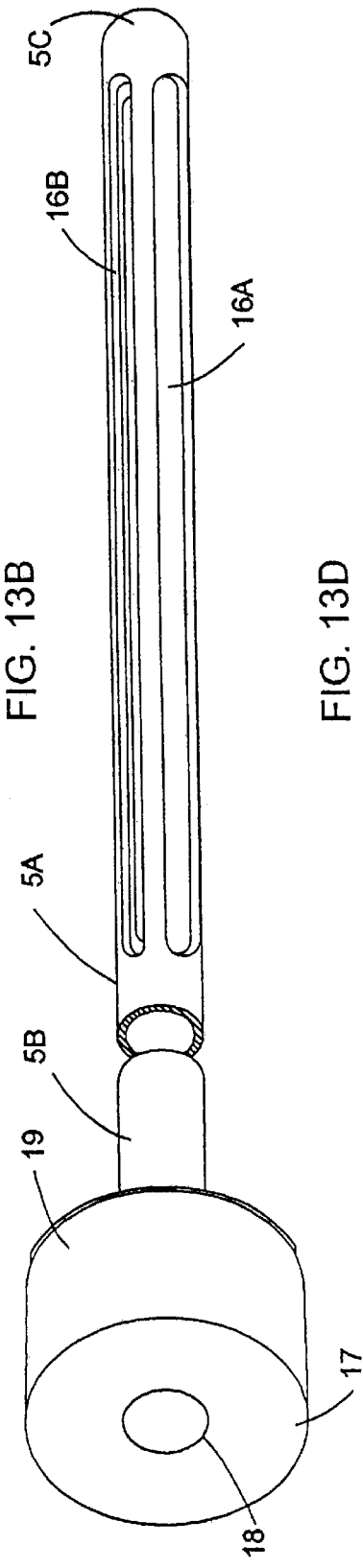
FIG. 13D

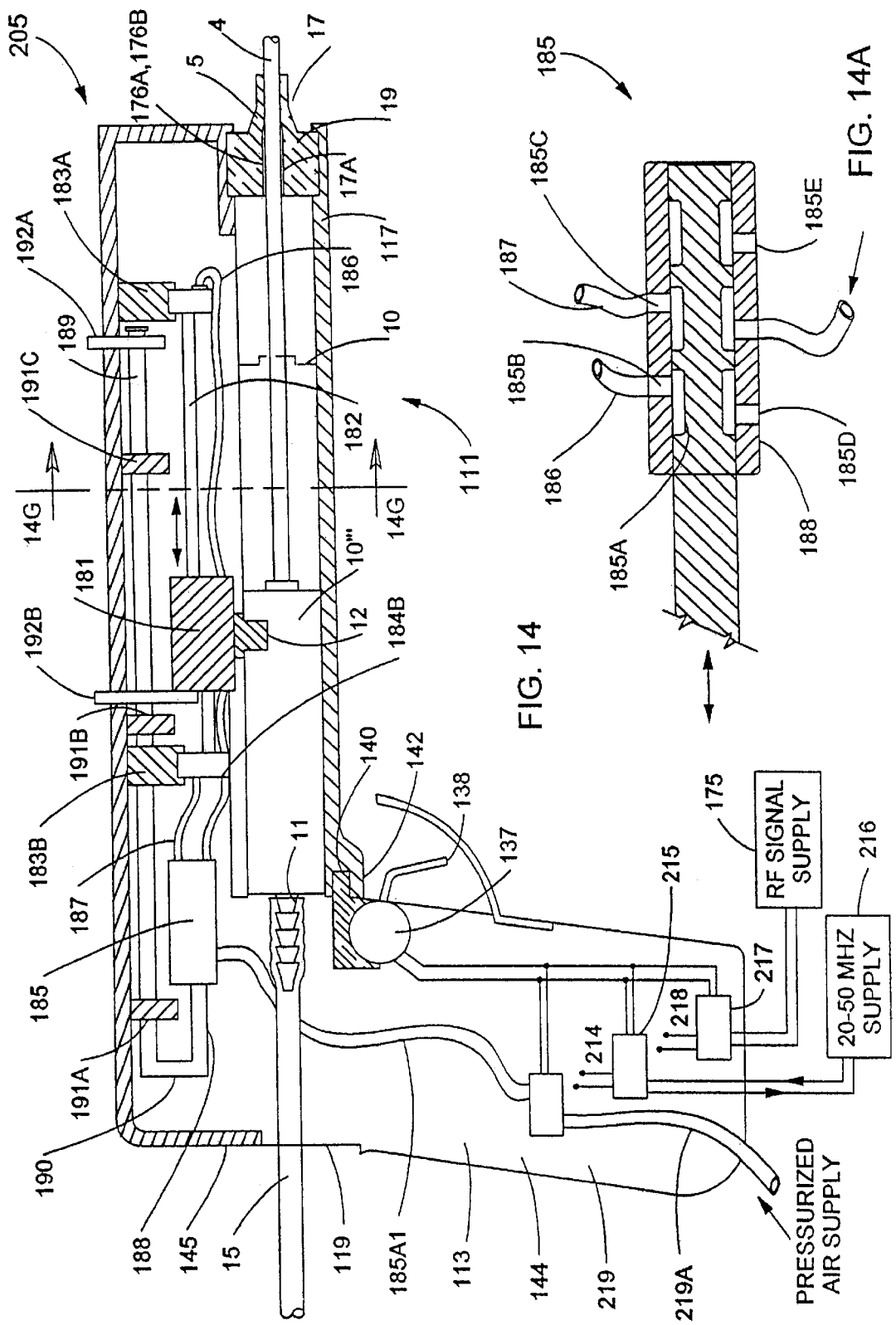

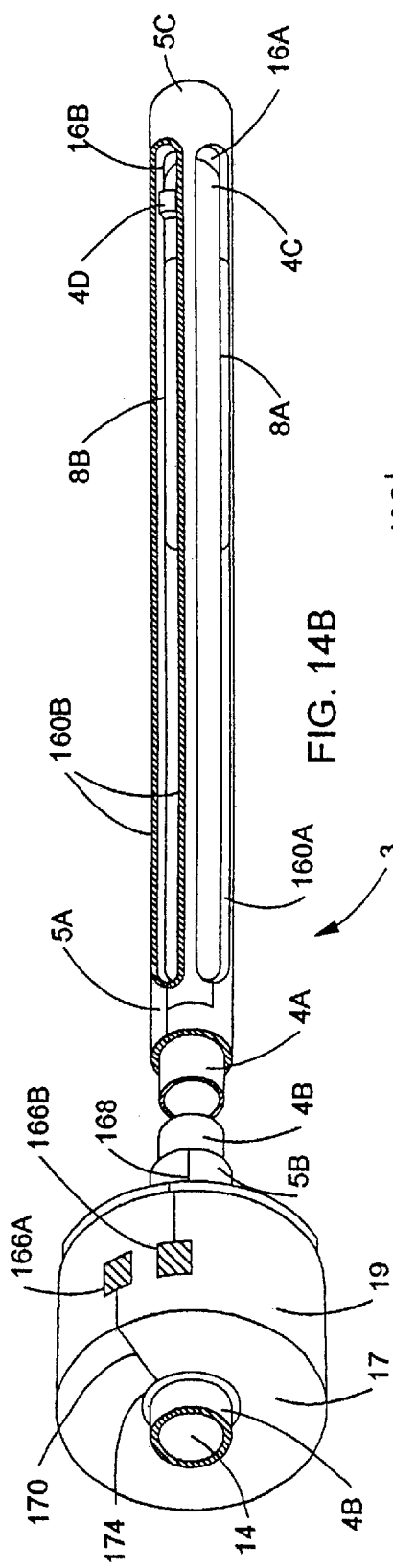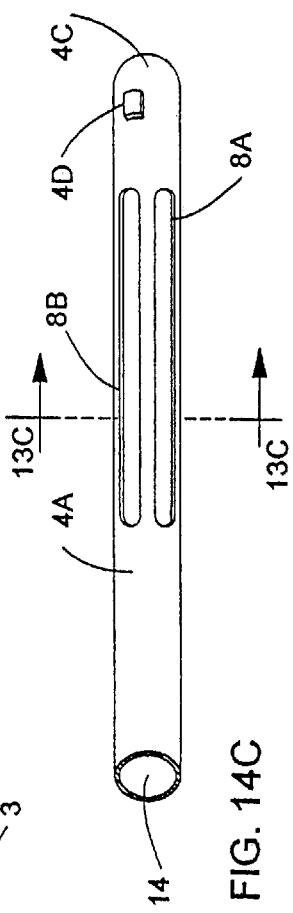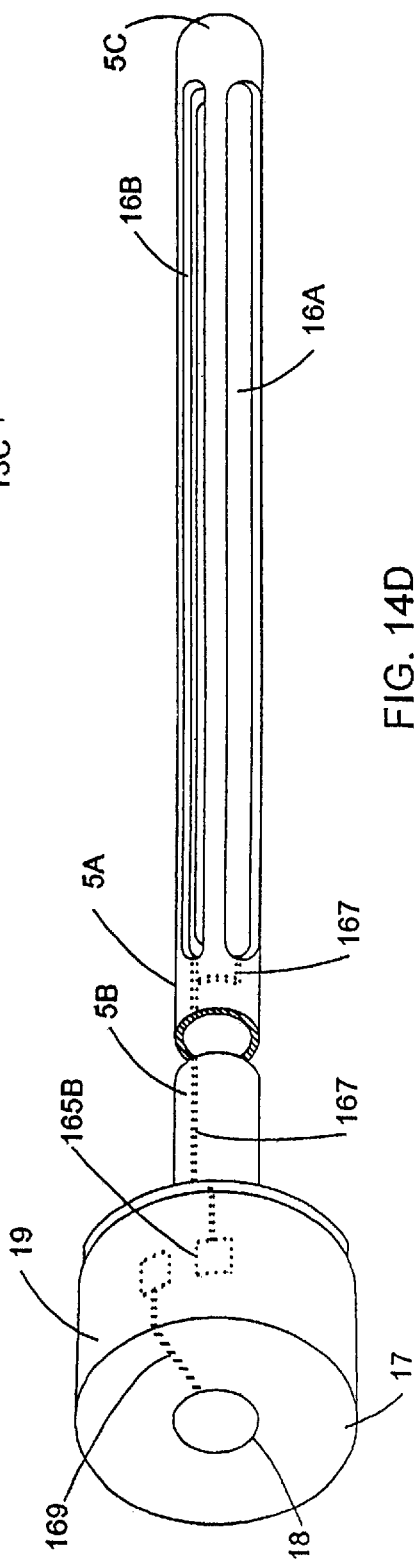
FIG. 14B
FIG. 14C
FIG. 14D

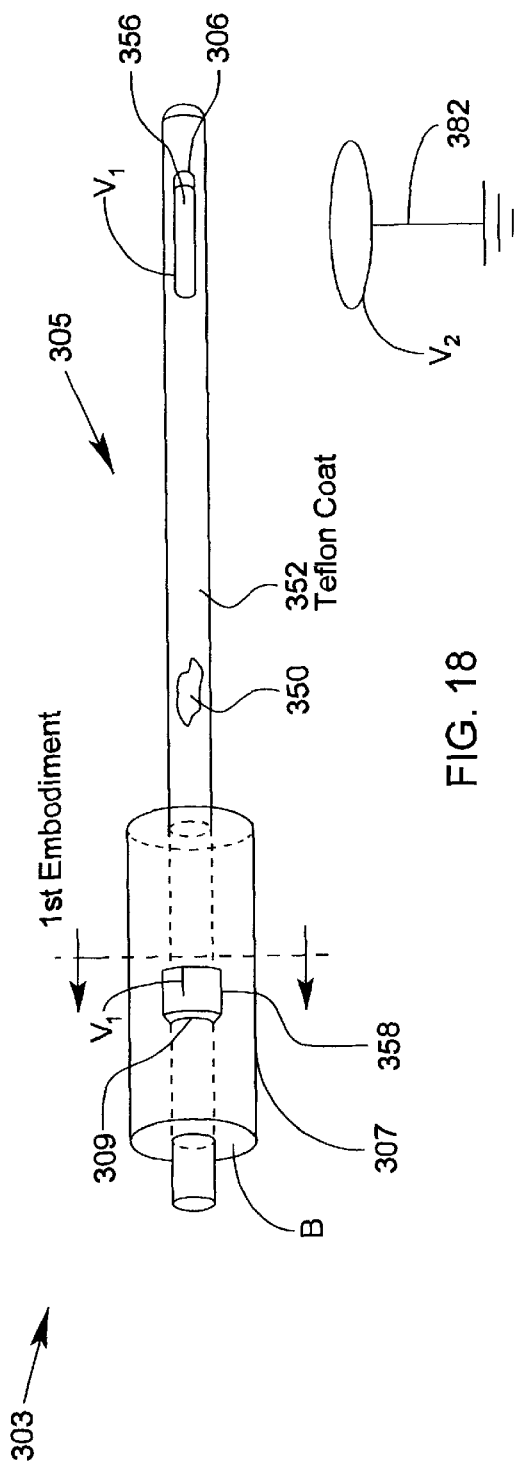
FIG. 18
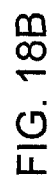
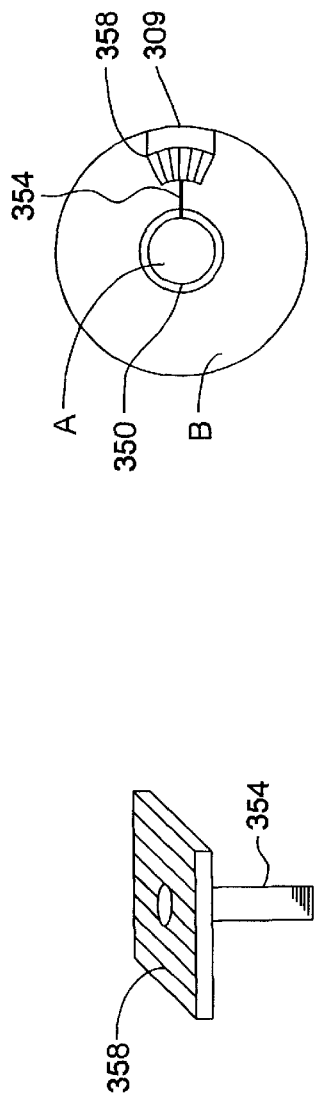
FIG. 18B
FIG. 18A

POWER-ASSISTED LIPOSUCTION INSTRUMENT WITH CAUTERIZING CANNULA ASSEMBLY

RELATED CASES

The present Application is a Continuation-in-Part of application Ser. No. 08/882,927 filed Jun. 26, 1997, now U.S. Pat. No. 5,795,323 which is a Continuation of application Ser. No. 08/307,000 filed Sep. 16, 1994, now U.S. Pat. No. 5,643,198, which is a Continuation of application Ser. No. 07/627,240 filed Dec. 14, 1990, now U.S. Pat. No. 5,348,535. Each said Application is incorporated herein by reference as if set forth in its entirety.

FIELD OF INVENTION

The present invention relates generally to a method and apparatus for performing liposuction, and more particularly to a method and apparatus for performing liposuction in a mechanically assisted manner using powered expedients.

BRIEF DESCRIPTION OF THE PRIOR ART

Suction lipectomy, commonly known as liposuction or lipoxheresis, is a well known surgical procedure used for sculpturing or contouring the human body to increase the attractiveness of its form. In general, the procedure involves the use of a special type of curet known as a cannula, which is operably connected to a vacuum source. The cannula is inserted within a region of fatty tissue where removal thereof is desired, and the vacuum source suctions the fatty tissue through the suction aperture in the cannula and carries the aspirated fat away. Removal of fat cells by liposuction creates a desired contour that will retain its form.

Presently, there are two widely accepted techniques of liposuction and each may be practiced using a conventional liposuction cannula. The first and most common method proposed by Yves-Gerard Illouz and described in the paper "Illouz's Technique of Body Contouring by Lipolysis" in Vol. 3, No. 3, July 1984 of Clinics in Plastic Surgery, involves making regular tunnels at a depth of at least 1 centimeter under the skin. According to this method, one or two insertions are made, with radial excursions of the cannula into the fatty tissue of the patient. The result is a multitude of concomitant sinuses formed below the subcutaneous fatty tissue, leaving intact as far as possible the connections between the skin and underlying tissue, thereby retaining the blood vessels, the lymphatics and the nerve endings. The second method is the original liposuction procedure proposed by U. K. Kesselring, described in "Body Contouring with Suction Lipectomy," in Vol. 11, No. 3, July 1984, Clinics in Plastic Surgery. According to the technique, an entire layer of regular, deep fat is removed by aspiration through the cannula, leaving a smooth, deep surface of the residual panniculus. The space thus created is then compressed, optimally followed by skin retraction.

Both of these prior art liposuction techniques require that the surgeon push and pull the entire cannula back and forth almost twenty times for each insertion made. Typically, twenty to thirty tunnels are made. This is necessary to ensure even removal of fat in the targeted region. During this procedure, the surgeon typically massages the flesh in the area of the aperture in the cannula, while at the same time. thrusting the rod in and out of the tunnel. Due to the trauma involved during the procedure, the patient's skin turns black and blue for several weeks. Due to the physically exacting nature of the procedure, the surgeon typically comes out of an operating room extremely tired and suffers from muscular fatigue which prevents him from performing, for some time thereafter on the delicate operations involved in ordinary plastic surgery.

Recently, the use of a "guided cannula" has been proposed by R. de la Plaza, et al., described in "The Rationalization of Liposuction Toward a Safer and More Accurate Technique," published in vol. 13, Aesthetic Plastic Surgery, 1989. According to the technique, a cannula is used in conjunction with an outer guide sheath through which the cannula can slidably pass while held in place by the handle portion of the guide sheath. Once the cannula and its sheath have been introduced into the fatty tissue, the sheath guide remains in the tunnel and guides successive introductions of the cannula, keeping it in the same tunnel. While the use of this liposuction technique offers some advantages over the conventional unguided liposuction cannulas, the guided cannula nevertheless suffers from several significant shortcomings and drawbacks. In particular, the guided cannula requires manually thrusting the cannula through the guide sleeve repeatedly for each tunnel. Although this is a less physically demanding procedure, the surgeon must thrust the cannula even more times through each tunnel to achieve the desired effect and hence is still easily fatigued and prevented from performing, for some time thereafter, delicate operations involved in ordinary plastic surgery.

In an attempt to solve the above-described problem, U.S. Pat. Nos. 4,735,605 and 4,775,365 and 4,792,327 to Swartz disclose an assisted lipectomy cannula having an aspiration aperture which effectively travels along a portion of the length of the cannula, thereby obviating the necessity of the surgeon to repeatedly push the cannula in and out of the patient's subcutaneous tissue where fatty tissue is to be removed. While this assisted lipectomy cannula can operate on either air or electric power, it nevertheless suffers from several significant shortcomings and drawbacks. In particular, the device requires an outer tube with an elongated slot and an inner tube having a spiral slot which must be rotated inside the outer tube to effectuate a traveling aspiration aperture. In addition to the device's overall construction posing difficulties in assembly, cleaning and sterilization, use with a variety of cannulas and highly effective fat aspiration does not appear possible.

Accordingly, there is a great need in the art for a mechanically assisted lipectomy cannula which overcomes the shortcomings and drawbacks of prior art lipectomy apparatus.

OBJECTS AND SUMMARY OF THE PRESENT INVENTION

Thus, it is a primary object of the present invention to provide an improved method and apparatus for performing liposuction which assists the surgeon in the removal of fat and other subcutaneous tissue (such as but not restricted to gynecomastia) from surrounding tissue, with increased control and without promoting physical fatigue.

It is another object of the present invention to provide such apparatus in the form of a hand-holdable liposuction instrument having a cannula assembly, in which the location of the aspiration aperture is periodically displaced as the inner or outer cannula undergoes sliding movement relative to the hand-holdable housing.

It is a further object to provide such a liposuction instrument in which the rate of reciprocation and the amount of excursion of the aspiration aperture, are selectively adjustable by the surgeon during the course of operation.

An even further object the present invention is to provide such a liposuction instrument which can be driven by air or electricity.

A further object of the present invention is to provide such a liposuction instrument, in which the cannula assembly can be simply detached from the hand-holdable housing for ease of replacement and/or sterilization.

An even further object of the present invention is to provide an improved method of performing liposuction, in which one of the cannulas of the cannula assembly is automatically reciprocated back and forth relative to the hand-holdable housing, to permit increased control over the area of subcutaneous tissue where fatty and other soft tissue is to be aspirated.

Another object of the present invention is to provide a power-assisted liposuction instrument, wherein means are provided along the cannula assembly to effecting hemostasis during liposuction procedures and the like.

Another object of the present invention is to provide such power-assisted liposuction instrument, wherein the hemostasis means is realized using RF-based electro-cauterization.

Another object of the present invention is to provide such a power-assisted liposuction instrument, wherein RF-based electro-cauterization is carried out by providing electro-cauterizing electrodes along the cannula assembly and supplying to these electrodes, a RF signal of sufficient power to achieve electro-coagulation and thus hemostasis during liposuction procedures.

Another object of the present invention is to provide such a power-assisted liposuction instrument, wherein the outer cannula is realized from a non-conductive material and electro-cauterizing electrode elements are inserted within the aspiration apertures thereof and electrical wiring embedded along the outer cannula and connected to a contact pad embedded within the base portion thereof, and wherein the inner cannula is made from an electrically conductive material which establishes electrical contact with contact brushes mounted within the central bore of the base portion of the inner cannula.

Another object of the present invention is to provide such a power-assisted liposuction instrument, wherein RF supply and return signals are coupled to the cannula assembly by way of the base portion of the outer cannula.

Another object of the present invention is to provide a power-assisted liposuction instrument, wherein RF-based electro-cauterization is realized using electrically conductive inner and outer cannulas which are electrically isolated by way of thin Teflon coatings applied to the outer surface of the inner cannula and/or the interior surface of the outer cannula.

Another object of the present invention is to provide a power-assisted liposuction instrument, wherein ultrasonic energy of about 40 kHz is coupled to the inner cannula in order to effect protein coagulation about the aspiration apertures and thus achieve electro-cauterization (is hemostasis) during liposuction procedures.

Another object of the present invention is to provide such a power-assisted liposuction instrument, wherein such ultrasonic energy is produced by piezoelectric crystals embedded within the base portion of the inner cannula and driven by electrical signals having a frequency of about 50 kHz.

Another object of the present invention is to provide such a liposuction instrument, wherein the electrical drive signals are supplied to the piezoelectric transducers by way of a pair of electrically conductive rails embedded within the interior surface of the cannula cavity of the hand-holdable housing of the liposuction device.

Another object of the present invention is to provide a way of carrying out RF-based cauterization within a cannula assembly, wherein the operating surgeon is enabled to perform lipolysis by driving the piezo-electric transducers within the base portion of the inner cannula with signals in the frequency range of about 20–25 kHz.

These and other objects of the present invention will become apparent hereinafter.

BRIEF DESCRIPTION OF THE DRAWINGS

For a fuller understanding of the objects of the present invention, reference is made to the detailed description of the illustrative embodiments which are to be taken in connection with the accompanying drawings, wherein:

FIG. 2A is a perspective, partially broken away view of the electro-cauterizing cannula assembly of the present invention installed in the liposuction instrument of FIGS. 1A through 8C, in which the electrically-conductive inner cannula adapted to freely undergo sliding movement within the stationary electrically non-conductive outer cannula while electro-cauterization is performed about the aspiration apertures thereof under the control of the surgeon;

FIG. 2B is a perspective view of the distal end of the inner cannula shown in FIGS. 1A, 1B and 2A;

FIG. 2C is a cross-sectional view of the electrically-conductive inner cannula taken along line 2C—2C of FIG. 2B;

FIG. 2D is a perspective, partially broken away view of the electrically non-conductive outer cannula shown in FIGS. 1A, 1B and 2A;

FIG. 2E is a cross-sectional view of the electro-cauterizing cannula assembly taken along line 2E—2E of FIG. 2A;

FIG. 3A is a plan view of a cauterizing electrode of the present invention adapted for insertion within the elongated aperture of the electrically non-conducting outer cannula;

FIG. 3A1 is an elevated side view of the cauterizing electrode of the present invention taken along line 3A1—3A1 of FIG. 3A;

FIG. 3A2 is an elevated side view of the cauterizing electrode of the present invention taken along line 3A2—3A2 of FIG. 3A1;

FIG. 3B is a perspective view of the electrically-conductive collar and brush device of the present invention which inserts with the central bore formed in the base portion of the electrically non-conductive outer cannula of the present invention shown in FIG. 2D;

FIG. 3B1 is a cross-sectional view of the electrically-conductive collar and brush device of the present invention taken along line 3B1—3B1 of FIG. 3B;

FIG. 4B is a cross-sectional view of a portion of the liposuction device of

FIG. 4A, illustrating an alternative inner cannula retention means;

FIG. 6A is a cross-sectional view of another embodiment of the liposuction device of the present invention, illustrating the use of a pair of gas driven piston-type motors and a mechanically-operated gas flow control device disposed in its first state of operation;

FIG. 6B is a cross-sectional view of the liposuction device of the present invention taken along line 6B—6B of FIG. 6A;

FIG. 6C is a perspective view of the preferred embodiment of the mechanically-operated gas flow control device illustrated in FIG. 6A;

FIG. 6D is a cross-sectional view of the gas flow control device of the present invention taken along line 6D—6D of FIG. 6C.

FIG. 7A is a perspective, partially broken away view of a snap-fit type inner cannula intended for use with the liposuction device of FIG. 4A;

FIG. 7B is a cross-sectional view of the outer cannula of the present invention taken along lines 7B—7B of FIG. 7A;

FIG. 8 is a perspective, partially broken away view of a snap-fit type outer cannula intended for use in connection with the liposuction device of FIG. 4A;

FIG. 9A is a plan cross-sectional view of another embodiment of the liposuction device of the present invention, having a hand-holdable housing realized in the form of a pistol-shaped structure having detachable barrel and handle portions;

FIG. 9B is a cross-sectional, partially broken away view of the liposuction device of the present invention taken along line 9A—9B of FIG. 9A, showing the cam mechanism of the present invention;

FIG. 9C is an elevated cross-sectional view of the liposuction device of the present invention, taken along line 9C—9C of FIG. 9A, showing the inner cannula disposed at a first position within the cannula cavity of the hand-holdable housing, and the rotary motor and speed control unit in the handle portion thereof;

FIG. 9D is a cross-sectional view of a portion of the inner cannula excursion control means shown in FIGS. 9B and 9C;

FIG. 9E is a cross-sectional view of the liposuction device of the present invention taken along line 9E—9E of FIG. 9A, showing the rotary drive wheel of the cam mechanism in operable association with the actuation element which projects through the cannula cavity and is engaged in the slotted base portion of the inner cannula, and also showing in phantom lines the cover panel of the barrel portion disposed in an open configuration permitting insertion or removal of the inner and outer cannulas of the present invention;

FIG. 9F is an elevated partially broken away rear view of the barrel portion of the liposuction device taken along line 9F—9F of FIG. 9A;

FIG. 10 is a cross-sectional view of another illustrative embodiment of the liposuction device of the present invention, wherein a liposuction device of the present invention is provided, having a double-acting air-powered cylinder with a magnetically-coupled actuator and the electro-cauterizing cannula assembly of the present invention is installed;

FIG. 10A is a cross-sectional schematic diagram of the air flow control device employed in the liposuction device shown in FIG. 10, in which the control valve thereof is mechanically linked to the reciprocating piston contained within the cylinder-style reciprocator within the housing of the liposuction device;

FIG. 11A is a perspective, partially broken away view of the electro-cauterizing cannula assembly of the present invention installed in the liposuction instrument of FIG. 10, in which the electrically-conductive inner cannula is adapted to freely undergo sliding movement within the stationary electrically non-conductive outer cannula while electro-cauterization is performed about the aspiration apertures thereof under the control of the surgeon;

FIG. 11B is a perspective view of the distal end of the inner cannula shown in FIG. 11A;

FIG. 11C is a cross-sectional view of the electrically-conductive inner cannula taken along line 11C—11C of FIG. 11B;

FIG. 11D is a perspective, partially broken away view of the electrically non-conductive outer cannula shown in FIG. 11A;

FIG. 11E is a cross-sectional view of the electro-cauterizing cannula assembly taken along line 11E—11E of FIG. 11A;

FIG. 12A is a plan view of a cauterizing electrode of the present invention adapted for insertion within the elongated aperture of the electrically non-conducting outer cannula shown in FIG. 11;

FIG. 12A1 is an elevated side view of the cauterizing electrode of the present invention taken along line 12A1—12A1 of FIG. 12A;

FIG. 12A2 is an elevated side view of the cauterizing electrode of the present invention taken along line 12A2—12A2 of FIG. 12A1;

FIG. 13A is a prospective, harshly broken away view of the electrically-conductive outer cannula employed in an alternative embodiment of the electro-cauterizing cannula assembly utilizable in the liposuction device of the present invention with suitable modifications;

FIG. 13B is a prospective view of a distal end of the inner cannula shown in FIG. 13A;

FIG. 13C is a cross-sectional view of the electrically conductive inner cannula taken along line FIG. 13C—13C of FIG. 13A;

FIG. 13D is a prospective harshly broken away view of the electrically conductive outer cannula shown in FIG. 13A, over which an electrically insulating coating such as Teflon is applied to the exterior surface thereof;

FIG. 14 is a cross-sectional schematic diagram of an alternative embodiment of the electro-cauterizing liposuction instrument of the present invention, wherein the reciprocation means is realized using a cylinder-style actuator powered by a supply of pressurized air;

FIG. 14A is a schematic cross-sectional view of the airflow control device employed within the liposuction instrument of FIG. 14;

FIG. 14B is a prospective, harshly broken away view of the electrically-nonconductive outer cannula employed in alternative embodiment of the electro-cauterizing cannula assembly utilized in the liposuction instrument of FIG. 14;

FIG. 14C is a prospective view of a distal end of the inner cannula shown in FIG. 14B;

FIG. 14D is a prospective harshly broken away view of the electrically nonconductive outer cannula shown in FIG. 14B, over which an electrically insulating coating such as Teflon is applied to the exterior surface thereof;

FIG. 18 is a perspective view of a first illustrative embodiment of the monopolar electro-cauterizing cannula assembly of the present invention shown removed from the hand-supportable device of FIG. 15, wherein an electrically-insulative outer coating is applied over an electrically conductive cannula structure that is electrically connected to the active lead of a unipolar electro-cautery power supply unit when the cannula assembly is installed within the hand-supportable device and the device is electrically connected to the power supply unit by way of any electrical cable;

FIG. 18A is a perspective view of the electrically-conductive contact element installed in the notch structure of the cannula assembly, for establishing electrical contact between the cannula assembly and the power source in the hand-held housing;

FIG. 18B is a cross-sectional view of the base portion of the cannula assembly shown in FIG. 18, taken along line 18B—18B drawn therein.

DETAILED DESCRIPTION OF THE ILLUSTRATED EMBODIMENTS

Figure 1A:
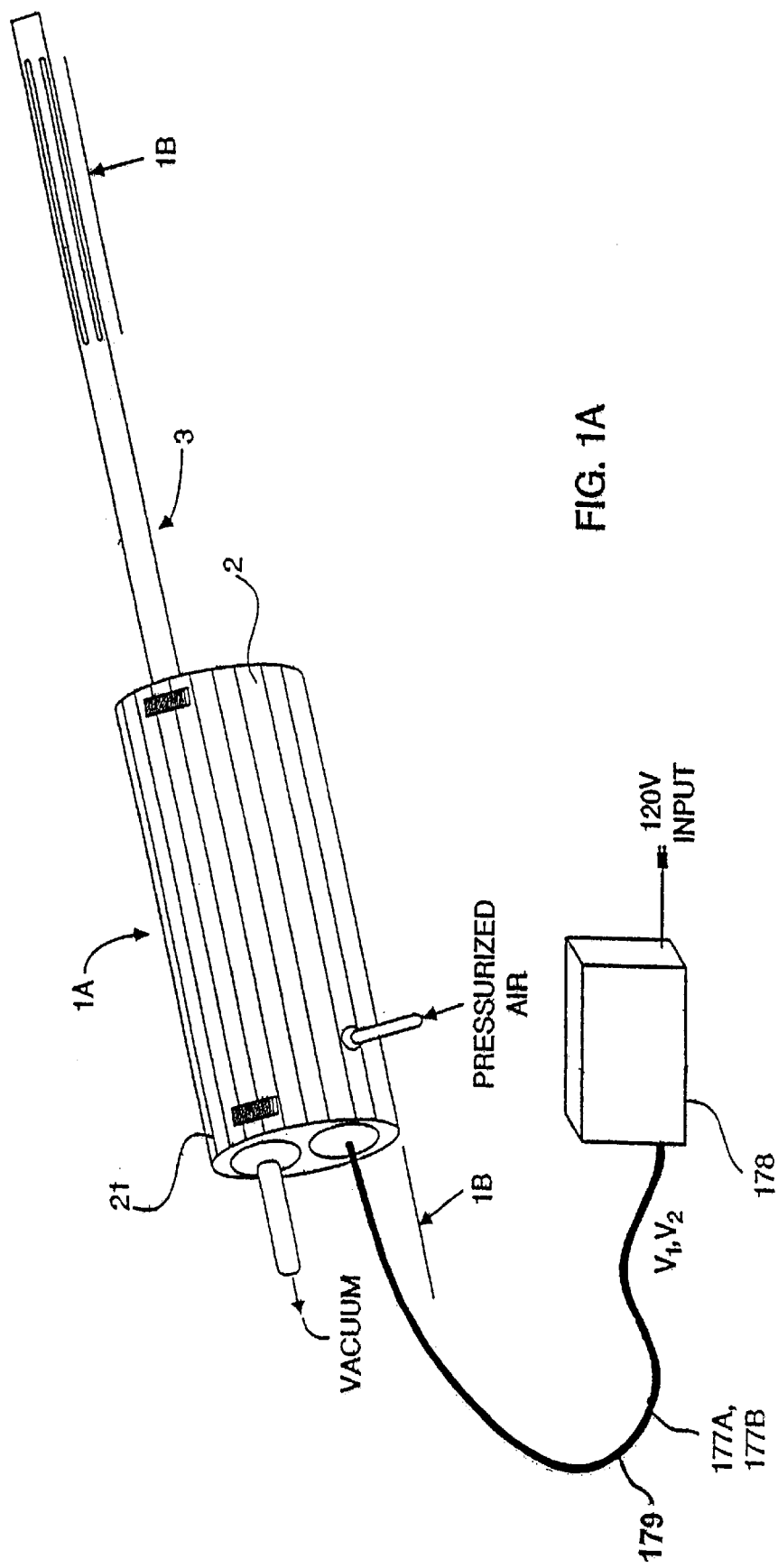
FIG. 1A is a perspective view of a first embodiment of the liposuction device of the present invention.

With reference to FIGS. 1A through 3D, the first embodiment will be described. In general, liposuction device 1A comprises hand-holdable housing 2, a detachable electro-cauterizing cannula assembly 3 having inner and outer cannulas 4 and 5, and a reciprocation means 6 for causing inner cannula 4 to reciprocate relative to outer cannula 5, which is stationarily disposed with respect to housing 2. This arrangement effectuates periodic displacement of the general location of aspiration along the cannula assembly through the reciprocating movement of inner cannula 4 while permitting electro-cauterization of aspirated tissue during operation of the liposuction device.

As illustrated in greater detail in FIGS. 1B, and 2A through 2E, the electro-cauterizing cannula assembly 3 of the present invention comprises an electrically-conductive inner cannula 4 and an electrically non-conductive outer cannula 5, each comprising hollow inner and outer tubes with distal and proximal ends 4A, 4B and 5A, 5B, respectively.

As shown in FIGS. 2B and 2C, the outer cannula 5 comprises a hollow outer tube having a distal and 5 comprises a hollow outer tube having a distal end 5A and a proximal end 5B. Four outer aspiration (i.e., suction) apertures generally indicated by reference numerals 8A, 8B, 8C and 8D are provided on the distal end of the inner cannula. As shown, elongated apertures 8A, 8B, 8C and 8D terminate at a predetermined distance away from outer cannula tip 5C, which is essentially blunt for purposes of safety. In general, the length of each of these elongated outer apertures is substantially longer than the longitudinal extent of each respective inner aperture. In the illustrated embodiment, the ratio of these lengths is about 1 to 4; however, in other embodiments, this ration may differ as desired or required in a given application. In a typical embodiment, the length of these elongated outer apertures would be within the range of, for example, two to six inches, commensurate with the amount of displacement to be achieved by each inner aperture.

Figure 1C:
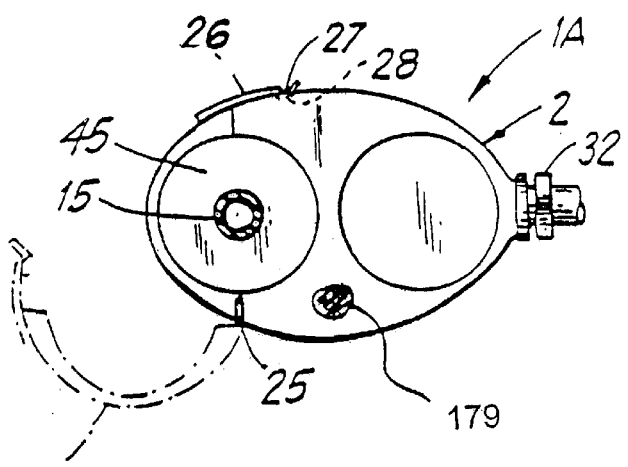
FIG. 1C is an elevated end view of the liposuction device of the present invention illustrated in FIG. 1A, showing the electro-cauterizing cannula assembly thereof retained within the cannula cavity of its hand-holdable housing, and alternatively with the hingedly connected housing cover panel disposed in an open position for removal of the cannula assembly therefrom.
Figure 1B:
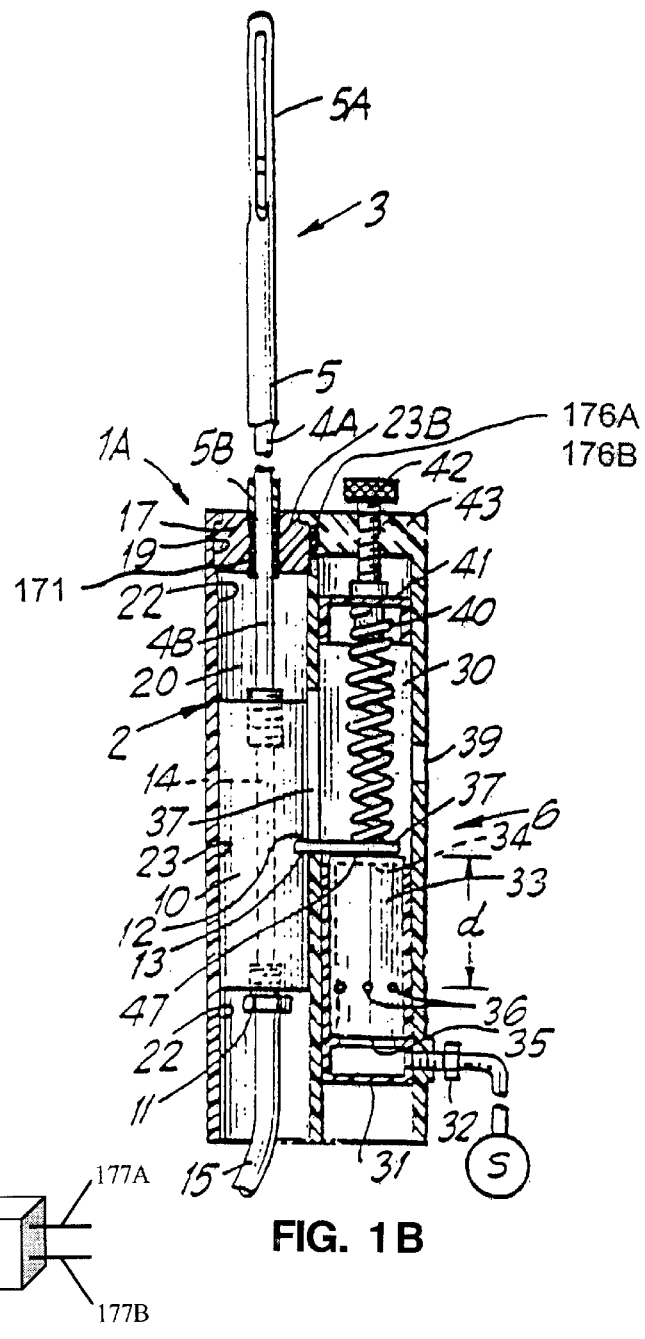
FIG. 1B is a cross-sectional view of the liposuction device of the present invention taken along line 1B—1B of FIG. 1A.

As illustrated in FIG. 1B, an outer cannula base 17 extends from the proximal end of outer tube 5. The outer cannula base 17 comprising a cylindrical structure having a central bore 18, through which distal tip 4C and body of inner cannula 4 can freely pass. The outer cannula base 17 of the illustrative embodiment includes a flanged portion 19 which fits within an annular recess 18 formed in cannula cavity 20 of the hand-holdable housing.

As shown in FIG. 2B, an inner cannula base 10 extends from the proximal end of inner tube 4. As shown, the inner cannula base 10 comprises a cylindrical structure having an outlet port 11 formed in its remote end. The inner cannula base 10 of the illustrative embodiment includes a notch or slot 12 formed in its central most portion. As will be described in greater detail hereinafter, notch 12 functions to releasably receive an extensional portion 13 of actuation element 37, in order to actuate reciprocation of inner cannula 4 within housing 2. As illustrated in FIG. 2B, inner cannula 4 has a continuous passageway 14 which extends from inner aspiration opening 9 to outlet port 11. As shown in FIGS. 2B and 2C, the inner aspiration apertures originate between the distal tip portion 4C. As shown, elongated apertures 16A, 16B, 16C and 16D terminate at a predetermined distance away from outer cannula tip 5C, which is essentially blunt for purposes of safety. In general, the length of each of these elongated inner apertures is substantially longer than the longitudinal extent of each respective outer aperture. In the illustrated embodiment, the ratio of these lengths is about 1 to 4; however, in other embodiments, this ratio may differ as desired or required in a given application. In a typical embodiment, the length of these elongated apertures would be within the range of, for example, two to six inches, commensurate with the amount of displacement to be achieved by each outer aperture with its electro-cauterizing element.

While not shown, a conventional vacuum source is connected to outlet port 11, preferably using optically transparent, semi-flexible tubing 15. With this arrangement, fatty tissue, aspirated fat tissue can be suctioned through apertures 8A, 8B, 8C and 8D and opening 9 and transported along passageway 14 to a reservoir device (not shown), operably associated with the vacuum source.

As illustrated in FIGS. 2A and 2E, electrically-conductive cauterizing electrodes 160A, 160B, 160C and 160D are inserted about the perimeter of outer aspiration apertures 16A, 16B, 16C, and 16D, respectively, and fastened thereto by snap-fitting, adhesive or like means. As shown in FIGS. 3A, 3A1 and 3A2, each electrically-conductive electrode comprises: a sidewall portion 161 which circumferentially extends about the perimeter of the respective aperture formed in the outer cannula; an opening 162 for permitting aspirated tissue and fat and the like to flow therethrough into the interior of the inner cannula; and a circumferential flange 163 substantially perpendicular to sidewall portion 161 and adapted to fit within a recessed groove 164 extending about the upper outer surface of the respective outer aspiration aperture formed in the electrically non-conductive outer cannula. In the illustrative embodiments, cauterizing electrodes 160A through 160D are made from stainless steel, brass, gold or any other electrically-conductive material that is suitable for contact with human tissue during liposuction and like surgical procedures.

As shown in FIG. 2D, the base portion of the outer cannula is provided with a pair of spaced apart recesses 165A and 156B for receiving and securing a first and second electrically-conductive contact pads 166A and 166B, respectively. A first groove 167 is formed within the outer surface of the outer cannula 5 and base portion 19 in order to receive a first length of electrical wiring 168 which establishes electrical contact between the set of cauterizing electrodes 160A through 160D and an electrically-conductive contact pad 166B. Similarly, a second groove 169 is formed within the outer surface of the outer cannula and base portion 19 in order to receive a second length of electrical wiring 170 which establishes electrical contact between the set of cauterizing electrodes 160A through 160D and second electrically-conductive contact pad 166A. A sealing material such as melted plastic can be used to close off the grooves 167 and 169 once the electrical wiring has been recessed within the groove. Alternatively, a thin, outer plastic cannula sleeve having an inner diameter slightly greater than the outer diameter of outer cannula 5 can be slid thereover and secured to the base portion thereof 19 using screw-threads, snap-fit fastening, ultrasonic-welding, adhesive or the like. When completely assembled, electrically-isolated contact pads 166A and 166B are mounted within the side walls surface of the base portion 1, as shown in FIG. 2A. It is understood, however, that contact elements 166A and 166B can be mounted elsewhere in the base portion of the outer cannula.

Figure 2F:
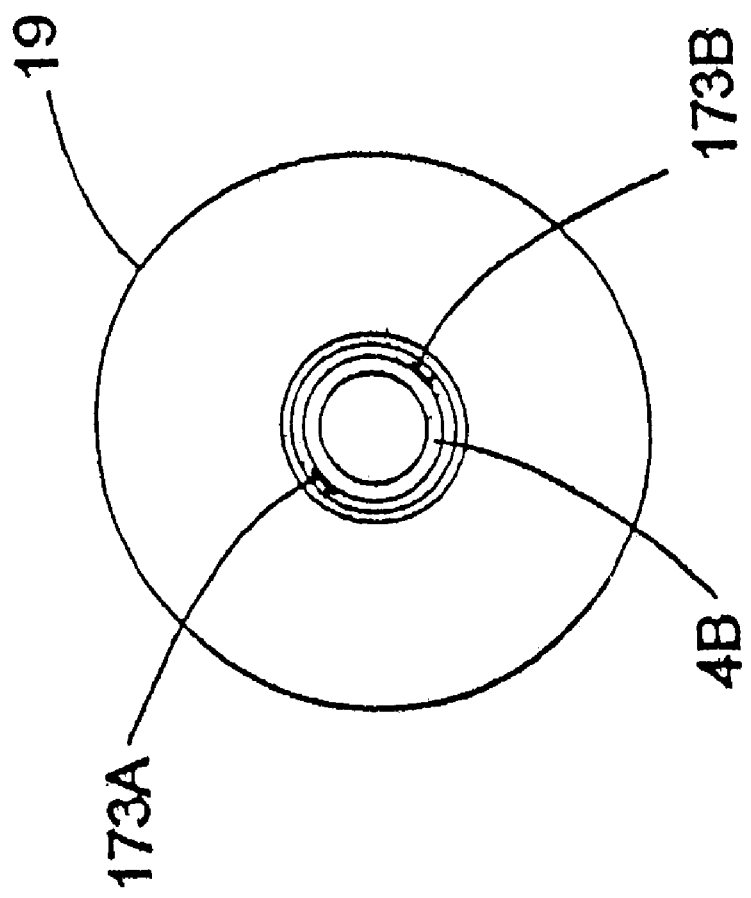
FIG. 2F is a cross-sectional view of the cannula base taken along line 2F—2F of FIG. 2A

As shown in FIGS. 2A, an electrically-conductive collar and brush device 17 shown in FIGS. 3B and 3B1 is inserted within the central bore formed in the base portion 19 of the electrically non-conductive outer cannula. The collar and brush device 171 comprises a cylindrical tube 172 made from electrically-conductive material (e.g., stainless steel) having an outer diameter that is slightly less than the diameter of the central bore formed through the base portion of the inner cannula. As shown in FIGS. 3B and 3B1, a pair of diametrically-opposed leaf-like electrical contact elements 173A and 173B project inwardly from the cylindrical walls of the device towards it s axial center. As best shown in FIG. 2F, the function of electrical contact elements 173A and 173B is to establish electrical contact between second contact pad 166A (on base portion 10) and electrically conductive inner cannula 4 when the inner cannula is slid through the central bore 18 of the outer cannula, as shown in FIG. 2A. A small annular flange 174 is formed on one end of the cylinder 172 to delimit the depth of its insertion.

As shown in FIG. 2E, the sidewall portion 161 of each cauterizing electrode 160A through 160D is of sufficient width ($w_g$) to provide a gap region 175 between (i) the electrically-conductive inner cannula 4 adjacent the electrode and (ii) the sidewall portion 161 thereof. Preferably, the width of each gap 175 is selected so as to minimize electrical arcing (i.e., sparking) between each electrode 160 and the electrically conductive inner cannula 4 when an RF signal of, for example, about 5000 kHz at 800 Volts is applied thereacross during electro-cauterization.

As shown in FIG. 1B, contact pads 166A and 166B establish electrical contact with conductive elements 176A and 176B and are embedded within recess 17. Electrically conductive elements 176A and 176B are connected to the RF supply and RF return signal terminals 177A and 177B, respectively, of bipolar RF signal generator 178. In the preferred embodiment, RF bipolar signal generator 178 is realized as the Instant Response™ Electrosurgical Generator (Model Force FX) by ValleyLab International, a subsidiary of Pfizer. Inc. This Electrosurgical Generator can be easily connected to the electro-cauterizing electrodes hereof by electrical cabling 179 in order to drive the same with bipolar outputs produced from the Electrosurgical Generator. Notably, the Instant Response Electrosurgical Generator 178 includes three bipolar output modes, namely: Low/Precise; Medium/Standard; and Macrobipolar. When operated in the Low and Medium bipolar modes, low output voltages are produced in order to prevent sparking across the electro-cauterizing electrodes.

When inner cannula 4 is installed within outer cannula 5, as shown in FIGS. 1A and 2A, inner apertures 8A, 8B, 8C, and 8D are able to freely slide along elongated outer apertures, 16A, 16B, 16C and 16D, respectively. Also, at each positioning of the inner cannula within the outer cannula, aspiration is permitted through each "effective"

aspiration (i.e., suction) aperture formed by the partial registration of each inner aspiration aperture with its corresponding outer aspiration aperture. Aspiration through these resulting effective aspiration apertures or openings, continues along passageway 14 and exits through outlet port 11. Consequently, the general location of aspiration along cannula assembly 3 is periodically displaced as inner cannula 4 is reciprocated relative to outer cannula 5, which is stationary with respect to the hand-supportable housing 2.

In order to maintain inner aspiration apertures 8A, 8B, 8C and 8D aligned with outer aspiration apertures 16A, 16B, 16C and 16D, respectively, and thus ensure partial registration therebetween, the distal end of the inner and outer tubes are provided with a keying system. In the illustrated embodiment, the keying system comprises a keying element 4D disposed on outer surface of the inner cannula, before distal tip 4C. Keying element 4D can be a rigid or flexible element that slides within an elongated outer aperture (e.g. 16B) and prevents axial rotation between cannulas 4 and 5 as they undergo relative reciprocation. To assemble cannula assembly 3, distal tip 4C of the inner cannula is inserted through bore 18 in outer cannula base 17 so that the distal end of inner cannula 4A is slidably received within outer cannula 5, as shown in FIG. 3A. In this configuration, keying element 4D is received and guided within elongated aperture 8B' as shown. In this general configuration, cannula assembly 3 is installed within cannula cavity 20 by first opening housing cover 21, shown in FIG. 1C. Then outer cannula base flange 17 is inserted within annular recess 19 and actuation extension 13 within inner cannula base notch 12. Thereafter, housing cover 21 is closed shut and liposuction device 1A is ready for operation. A conventional vacuum source is then connected to outlet port 11, preferably using optically transparent, semi-flexible tubing 15. With this arrangement, fatty tissue, aspirated through apertures 8A/16B, 8B/16B and 8C/16C and 8D/16D and opening 9, can be transported through passageway 14 to a reservoir device (not shown), operably associated with the vacuum source.

As shown in FIG. 1A, the gross geometry of housing 2 is preferably that of an ellipsoid, however, other geometries such as, for example, a cylindrical structure, can be used in practicing the present invention. Housing 2 contains cannula cavity 20, which extends along the entire longitudinal extent of the hand-holdable housing. In the illustrated embodiment, cannula cavity 20 has generally cylindrical bearing surfaces 22 which match the outer bearing surface 23 of inner cannula base 10, to permit sliding movement of inner cannula 3 within cavity 20. While cylindrical bearing surfaces have been selected in the illustrated embodiment, use of other forms of bearing surfaces (e.g., rectangular or triangular) are contemplated. To minimize friction, bearing surfaces 22 and 23 may be coated with a Teflon® or functionally equivalent coating, to facilitate easy sliding of inner cannula base 10 within cavity with low wear. As illustrated in FIG. 1B, cannula cavity 20 also includes annular recess 19, into which annular base flange 19 is adapted to be received in order to render the outer cannula essentially stationary with respect to hand-holdable housing 2.

As shown in FIG. 1B, electrical contact pads 176A and 176B are embedded within surface-recesses formed within the wall surfaces of the annular recess 19. Preferably, electrically-conductive contact pads 176A and 176B are made from electrically conductive material having a shaped which is similar to the shape of electrically conductive pads 166A and 166B that are embedded within the outer surface of the base portion of the outer cannula 5. When the cannula assembly of this embodiment is installed within the hand-holdable housing, the electrical contact pads 166A and 166B on the base portion of the outer cannula will automatically establish electrical contact pads 176A and 176B within recess 19, respectively. In this way, the RF supply and return voltages from RF signal generator 178 are automatically applied to the electro-cauterizing electrodes embedded within the cannula assembly of the present invention.

As illustrated in FIG. 1C, hand-holdable housing 2 is provided with a hinged cover 21. Hinged cover 21 allows cannula cavity 20 to be opened and accessed so that cannula assembly 3 can be selectively installed in cannula cavity 20 and removed therefrom as desired or required. Cover panel 21 has a semi-circular cross-sectional geometry and is connected to the remaining portion of housing 2 by a conventional hinge means 25. To secure cover panel 21 to the remainder of housing 2, a releasable locking means 26 is provided at the interface of hinge cover 21 and housing 2, as shown. Releasable locking means 26 can realized in a variety of ways, including, for example, using a spring biased lamp element 27 which engages in a notch 28 formed in the external surface of the remaining housing portion, as illustrated in FIG. 1C.

In general, there are numerous ways to effectuate reciprocation of inner cannula 4 within cannula cavity 20 and thus within stationary outer cannula 5. Examples of possible reciprocation means 6 include, but are not limited to, gas or electrically driven motor(s). In the embodiments illustrated in FIGS. 1A through 1C, FIGS. 4A through 6A, FIGS. 7 through 8A, FIGS. 6A through 6D, and FIGS. 10 through 14D, one or more gas driven piston-type motors are employed to realize the reciprocation means 6 within the liposuction instrument. In the embodiment illustrated in FIGS. 9A through 9F, a rotary-type motor is used to realize reciprocation means 6 of the present invention.

As illustrated in FIG. 1B, a piston-type motor 6 is mounted within a motor cavity 30 provided adjacent cannula cavity 20 of housing 2. Notably, this reciprocation means cavity 30 extends essentially parallel to cannula cavity 20 and along a substantial portion of the longitudinal dimension of hand-holdable housing as will become more apparent hereinafter. This unique spatial relationship between the cannula cavity and reciprocation means cavity within housing 20, ensures optional cannula displacement relative to longitudinal dimensions of the hand-holdable housing.

In general, motor 6 comprises a chamber housing 31 having a gas inlet port 32 and an inner chamber generally indicated by reference numeral 33. Slidably received within the inner chamber of housing 31 is a movable piston 34 having formed in the lower portion wall 35, one or more gas outlet ports 36. Mounted to the top portion of movable piston 34 is actuation element 37, whose extension 13 projects through longitudinally disposed slot 38 formed in the bearing wall surface 22 of cannula cavity 20. As shown in FIG. 1B, actuation extension 13 passing through slot 38, is received within notch 12 formed in inner cannula base 10 and operably associates inner cannula 3 with motor 6.

As illustrated in FIG. 1B, chamber housing 31 is fixedly disposed within motor cavity 30. Motor cavity 30 is also provided with at least one port 39 for ventilating to the ambient environment, gas released from inner chamber 33 upon movable piston 34 reaching it maximum displacement or excursion. Movable piston 34 is biased in the direction of chamber housing 31 by way of a spring biasing element 40. The compliance of spring biasing element 40 can be adjusted by moving the position of slidable wall 41 by rotating, for example, threaded element 42 passing through a portion 43 of housing 2, as shown. With this arrangement, adjustment of wall 41, closer to or farther from chamber housing 31, results in decreasing or increasing, respectively, the compliance of spring biasing element 40. This mechanism, in turn, provides a simple, yet reliable way in which to control the rate of reciprocation of movable piston 34, and thus the rate of reciprocation of inner cannula 3 relative to housing 2.

The manner of operation of piston-type motor 6 is described as follows. Gas, such as pressurized air or $N_2$ gas, is introduced under constant pressure to inlet port 32 of chamber housing 31. As the gas fills up the volume enclosed by the interior walls of movable piston 34 and chamber 33, inner chamber 33 begins to expand, forcing movable piston 34 upwardly against the biasing force of spring biasing element 40. When movable piston 34 is displaced sufficiently enough from chamber housing 31 so that gas within expanding chamber 33 can be released through gas exit port 39 to the ambient atmosphere, piston 34 will be forced back downwardly into chamber housing 31. The rate of the forced downward piston movement is inversely proportional to the compliance of spring biasing element 40. Subsequently, chamber 33 will again fill up with gas, piston 34 will again be displaced and gas subsequently vented, whereupon reciprocating displacement of piston 34 will be repeated again in a cyclical manner. Since movable piston 34 is operably connected with inner cannula base 10 by way of actuation element 37, this reciprocating movement of piston 34 results in reciprocating movement of inner cannula 3 within cannula cavity 20. further, this relative reciprocation between the inner cannula and the outer cannula results in periodic displacement of the effective aspiration apertures along the distal end portion of the cannula assembly.

As illustrated in FIG. 1B, the amount of excursion that piston 34 is permitted to undergo before gas venting and subsequent downward piston movement occurs, is determined by the distance "d" defined between gas output port 32 and top wall surface 47 of chamber housing 31. Atypical cannula excursion distance of about four inches, for example, will necessitate that the parameter d, defined above, be also about four inches.

Figure 4A:
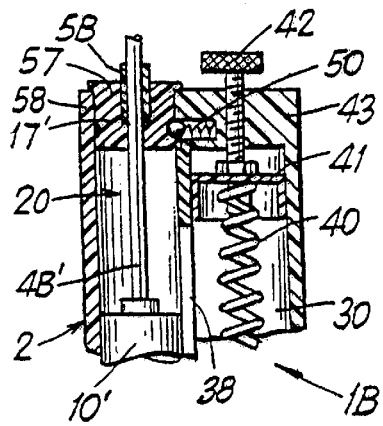
FIG. 4A is a cross-sectional view of a portion of another embodiment of the liposuction device of the present invention, illustrating an alternative outer cannula retention means.
Figure 4B:
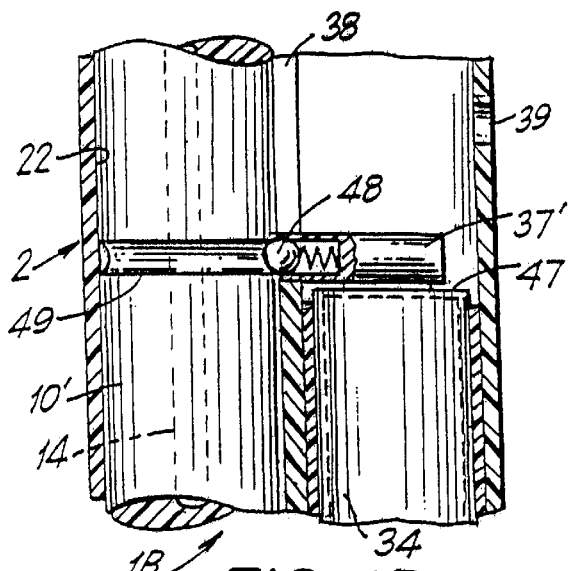

In FIGS. 4A and 4B, a second embodiment of the liposuction device of the present invention is shown. Liposuction device 1B has an alternative cannula assembly retention means while inhering all of the structural features of the first embodiment illustrated in FIGS. 1A through 1C. In particular, liposuction device 1B does not have a hingedly connected housing cover panel, and instead incorporates a snap-fit type cannula assembly retention mechanism. In accordance with this embodiment, actuation element 37' has an extension which is essentially flush with elongated slot 38 formed in cavity wall 22.

In FIGS. 4A and 4B, an alternative embodiment of the electro-cauterizing cannula assembly hereof is shown. This cannula assembly is similar to the above-described cannula assembly in all respectives except the extension on actuation element 37. In this alternative embodiment, the extension on actuation 37' is provided with a spring biased ball bearing 48 that projects slightly beyond cannula cavity wall surface 22. When inner cannula base 10' is pushed into cannula cavity 20 in the vicinity of actuation element 37', ball bearing 48 engages within indentation ring 49 circumferentially formed about inner cannula base 10'. Notably, spring biased ball bearing 48 functions as an engaging means for inner cannula base 10'.

As shown in FIG. 4A, the engaging means for outer cannula base 17' is also realized as a spring biased ball bearing 50 installed through cannula cavity wall 22. Outer cannula base 5' is provided with an annular flange 47 and indentation ring 49 circumferentially formed about outer cannula base 17'. As shown, annular flange 57 establishes surface to surface contact with peripheral surface 58 area of the housing when cannula base 5' is pushed into cannula cavity 20. In this position, ball bearing 50 engages within indentation ring 49 and a snap-fit engagement is established. This arrangement serves to retain both inner and outer cannulas 3' and 4 cannula cavity 20', in a releasable manner, as actuation element 37' is caused to reciprocate periodically. The outer cannula is simply removed from cannula cavity 20 by quickly pulling on outer cannula tube 5 with a modest degree of force, to overcome the bias force of engaged ball bearing 50. Similarly, the inner cannula is simply removed by quickly pulling on inner cannula tube 4' to over come bias force of engaged ball bearing 50. Advantageously, this cannula assembly retention mechanism can also provide a safety release feature, in that if inner cannula 4', for example, becomes snagged during an operation, it will disengage from the reciprocation means 6 if a proper spring biasing force is selected for ball bearing 50.

FIGS. 7A, 7B and 8 also show an electro-cauterizing cannula assembly according to the present invention which is adapted for use with liposuction instruments having cannula retention capabilities of the snap-in type described above. Notably, the elements which correspond to inner and outer cannulas illustrated in FIGS. 2A through 3B1, are indicated by similar reference numbers.

In the embodiment featured in FIGS. 7A and 7B, inner cannula base 10" has a deeply formed spherical indentation 52 which is adapted to receive ball bearing 48 mounted in the extension of in actuation element 37. To facilitate guiding ball bearing 48 into spherical indentation 52, a longitudinally extending groove 53 is formed in inner cannula base 10". Also, as shown, widened recess portions 53A and 53B are provided at opposite ends of groove 53 to facilitate initial insertion of ball bearing 48 in groove 53. When inner cannula base 10" is slid into cannula cavity 20, ball bearing 48 snaps into indentation 52 to establish a locked position. Biased ball bearing 48 engaged in spherical indentation 52 serves to retain inner cannula 5 within cannula cavity 20, while facilitating reciprocation of inner cannula 5 when actuation element 37' is caused to reciprocate.

Similar to the snap-fit inner cannula retention mechanism illustrated in FIGS. 7A and 7B, FIG. 8 shows outer cannula base 17" having a longitudinally extending groove 55. Also, as shown, widened recess portions 55A and 55B are formed at opposite ends of groove 55 to facilitate insertion of ball bearing 50 into spherical indentation 56. When outer cannula base 17" is slid into cannula cavity 20, ball bearing 50 snaps into spherical indentation 56 to establish a locked position. When this occurs, annular flange 57 will engage with outer peripheral surface 58, about circular access opening leading into cannula cavity, shown in FIG. 4A. Upon such engagement, outer cannula 5 is rendered stationary relative to hand-holdable housing 2. As with inner cannula 4, the outer cannula is simply removed from cannula cavity 20 by pulling on outer cannula tube 5 with a modest degree of force to overcome the bias force of engaged ball bearing 50.

Figure 5:
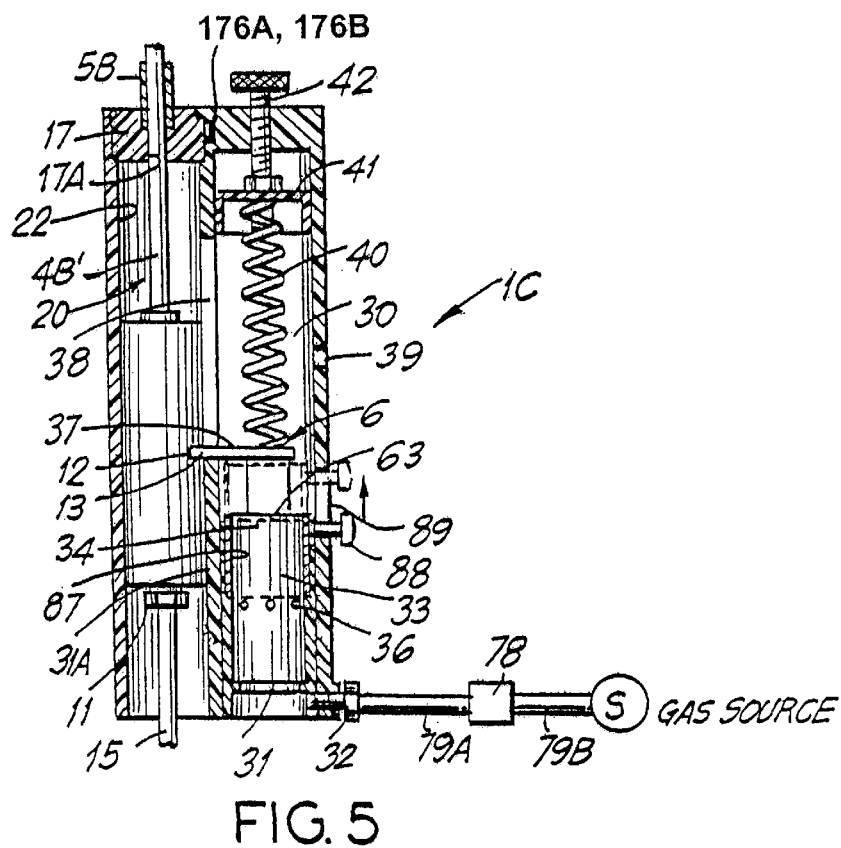
FIG. 5 is a cross-sectional view of another embodiment of the liposuction device of the present invention, illustrating a means for controlling the mount of excursion of the aspiration aperture along the cannula assembly.

In order to selectively adjust the amount of cannula excursion permitted during a liposuction operation, piston-type motor 6 can be modified, as shown in FIG. 5, to produce embodiment of the liposuction device of the present invention. As illustrated in FIG. 5, the basic structure of liposuction device 1C is similar to that shown in FIGS. 1A through 1C, except that a user-adjustable intermediate housing wall 88 is disposed between the inner walls 31A of chamber housing 31 and the outer walls 34A of movable piston 34. Intermediate housing wall 87 is operably associated with an excursion selection means realized as a slidable member 88 fixedly attached to the upper portion of intermediate housing wall 59. Preferably, slidable member 88 extends through a slot 89 formed in the wall of housing 2 and can be slid, for example, by movement of the surgeon's thumb. The function of intermediate housing wall 87 is to effectively raise the height of the chamber housing wall, and thus selectively increase distance d, defined, for example, as the distance between gas outlet port 32 in piston 34 and upper portion 63 of the chamber housing wall. In this way, movable piston 34 must undergo a larger displacement before compressed gas will be released and piston 34 permitted to be forced downwardly under the biasing force of biasing spring element 40.

As illustrated in the embodiment shown in FIG. 5, it is also possible to control the rate of reciprocation of the inner cannula by controlling the rate of gas flow entering chamber 33 of piston-type motor 6. This can be achieved using a conventional gas flow regulation device 78 inserted between source of gas "S" and inlet port 32 of chamber housing 31. As shown, tubing sections 79A and 79B are used to achieve fluid communication between these elements. Typically, cannula reciprocation rates will be in the range of 30 to 90 reciprocation cycles per minute, and the corresponding gas flow rates will depend on parameters including, for example, the compliance of biasing spring 40, the volumes of movable piston 34 and chamber housing 31, the cross-sectional diameter of gas inlet port 32, and the cross-sectional diameter of gas outlet ports 36 in the piston.

Referring to FIGS. 6A through 6D, there is shown another embodiment of the liposuction device of the present invention. In liposuction device 1F, the housing and cannula assembly are generally similar to those of the previously described embodiments, with the exception of several differences which will be described below.

As illustrated in FIG. 6A, a pair of piston-type motors 6A and 6B of the type generally indicated in FIGS. 1A through 1C and 5, are fixedly installed within respective motor cavities 30A and 30B of housing 2. Each piston-type motor 6A and 6B has a respective chamber housing and movable piston, indicated by 31A and 31B, and 34A and 34B, respectively. Actuation elements 37A and 37B are fixedly connected to respective pistons 34A and 34B and project through respective elongated slots 38A and 38B formed in cannula cavity wall 22; this is achieved, in a manner similar to that described in connection with the embodiments shown in FIGS. 1A through 1C, 4A, 4B and 5. While not shown in FIG. 6A, preferably a rod or bar is fixedly attached between actuation elements 37A and 37B in order to maintain them a fixed distance apart, and yet provide an operable connection between the inner cannula 41 and actuation elements 37A and 37B in the manner described below. As shown in FIG. 6B, this embodiment includes hinged cover panel 21 in a manner similar to that described in the embodiments of FIGS. 1A, 1C, 5, 6A and 8A.

As illustrated in FIG. 6A, inner cannula base 10''' has first and second receiving slots or notches 12A and 12B, into which extensions 13A and 13B of respective actuation elements 37A and 37B are received. Such operable connections between movable pistons 6A and 6B and inner cannula base 10''' enables inner cannula 4' to reciprocate relative to housing 2 when actuation elements 37A and 37B are caused to reciprocate relative to respective gas driven motors 6A and 6B.

In order to control the filling and venting of chambers 33A and 33B of the first and second piston motors, to effectuate cyclical reciprocating motion of actuation elements 37A and 37B and thus inner cannula 4', a mechnically-operated gas flow control device 90 is employed in operable association with an external source of pressurized gas (not shown), gas inlet ports 32A and 32B, and movable pistons 34A and 34B.

As illustrated in greater detail in FIGS. 6C and 6D, gas flow control device 90 comprises a shuttle valve housing or casing 91, having first and second shuttle chambers 92A and 92B. These shuttle chambers are separated by a shuttle valve member 93 which is fixedly attached to a slidable shaft 94. As illustrated, shuttle valve member 93 is slidable between two positions or states "A" and "B". In order to achieve this shaft 94 extends through bores 95A and 95B formed in shuttle chamber and walls 91A and 91B respectively, in which seals 96A and 96B are installed in a conventional manner. When the shuttle valve 93 is centrally disposed in casing 91 between states A and B, shaft ends 94A and 94B protrude equally beyond respective bores 95A and 95B.

Adjacent one end of cylindrical shuttle chamber side wall 98, a first gas exit port 89A is formed, whereas adjacent the other end of wall 98, a second gas exit port 98B is formed, as shown. At about intermediate the end walls, a gas inlet port 100 is formed in shuttle chamber side wall 98. A pair of annulus-shaped shuttle valve stops 101A and 101B are formed at opposite end portions of the interior surface of cylindrical wall 98. These stops 101A and 101B serve to limit sliding movement of shuttle valve 93 when shaft 94 is displaced in one of two possible axial directions by actuation elements 37A and 37B, respectively, as shown in FIG. 6A. As will be discussed in greater detail hereinafter, it is these actuation elements 37A and 37B which displace shaft 94 and thus shuttle valve 93 between one of two states, as movable pistons 34A and 34B are caused to reciprocate. Preferably, at least a portion of shuttle valve 93 is formed of a ferromagnetic material so that ferrous end walls 102A and 102B will attract ferromagnetic shuttle valve 93 and pull it against one of stops 101A and 101B and into gas flow state A or B, i.e., when shuttle valve 93 is brought into proximity therewith upon displacement of shaft 94 by one of actuation elements 37A and 37B. Peripheral side surfaces of shuttle valve 93 are provided with seals 103 to prevent gas leakage between shuttle chambers 92A and 92B.

As illustrated in FIG. 6A, first gas exit port 99A of device 90 is in a fluid communication with second chamber housing 31B by gas channel 104, whereas second gas exit port 99B is in fluid communication with first chamber housing 31A by gas channel 105. In the illustrated embodiment, gas inlet aperture 106 is formed through housing 2 and permits gas channel 107 to establish fluid communication between gas inlet port 100 and the external source of pressurized gas. Notably, chamber housings 31A and 31B, shuttle valve housing 91, gas channels 104, 105 and 107 can be realized as discrete elements, as shown, or alternatively as integrally formed elements which are part of the interior of the hand-holdable housing itself.

The principal function of gas flow control device 90 is to control the flow of gas to pistons 34A and 34B so that only one of the gas pistons is actively driven at a time, while the other is passively driven. The manner of operation of gas flow control device 90 in cooperation with the periodic displacement of pistons 34A and 34B, will now, be described.

Owing to the fact that shuttle valve 93 is magnetically biased to be in essentially one of two possible positions, or gas flow states, gas will initially be caused to flow into one of piston-chamber housings 31A or 31B, and cause its respective piston and actuation element to move away (i.e. protract) from its respective chamber housing. Only along a small portion of the piston excursion will shuttle valve shaft 94 and thus shuttle valve 93, be displaced within shuttle valve housing 91 as the actively driven piston is displaced upon buildup of pressurized gas within its respective chamber.

To illustrate this cyclical process, it will be assumed that gas flow control valve 90 is initially in state A, as shown in FIG. 6A. Here, piston 34A has reached its maximal displacement and pressurized gas within chamber 33A has been substantially vented through gas outlet port 26A and through ports 39A and 39B. In this position (state A), shuttle valve 90 is magnetically biased against stops 101B so that gas is caused to flow from the external gas source (not shown), through first shuttle chamber 93A and into second chamber housing 33B. With shuttle valve 92 in this state, gas pressure is allowed to build up in chamber 33B, displacing piston 34B and actuation element 37B to protract from second chamber housing 31B. Therewhile, inner cannula base 10′41 is caused to undergo an outwardly directed excursion within cannula cavity 20, commensurate with the active displacement of piston 34B. During piston excursion (i.e., travel) defined over length $L_1$, shuttle valve 93 remains in state A against stop 101B.

Then over piston excursion $L_2$, actuation element 37B contacts shaft end 94B and displaces shuttle valve 93 away from stop 101B to about mid-position in shuttle housing 91, approximately over input port 100, at which point, magnetic shuttle valve 93 is pulled toward ferrous plate 102A into state B and against stop 101A, as shown in FIG. 6A with phantom lines. At this phase in the cycle, piston 34A is fully retracted within chamber housing 31A, while piston 34B is fully protracted from chamber housing 31B and displaced a distance $L_3$ from the upper portion thereof (i.e., $L_3=L_1+L_2$). In State B, gas flow control device 50 directs the flow of pressurized gas from the external source, along channel 107, through second shuttle chamber 92B and along channel 105 and into piston chamber housing 31A.

Magnetically biased shuttle valve 93 remains in state B as chamber housing 31A fills with pressurized gas, expanding the chamber 33A and actively displacing piston 34 A away from chamber housing 31A, while causing piston 34B to passively retract back into its chamber housing 31B. All the while, inner cannula base 10′″, being operably associated with actuation elements 37A and 37B, undergoes a commensurate amount of inwardly directed excursion within cannula cavity 20. When piston 34B is displaced an amount of distance $L_4$, actuation element 37A contacts shaft end 94A and displaces shuttle valve 93 a small distance $L_5$, at which point, magnetic shuttle valve 93 is pulled towards ferrous plat 102B, back into state A and against stop 101B. At this phase in the cycle, piston 34B is fully retracted within chamber housing 31B while piston 34A is fully protracted from chamber housing 31A and displaced at a distance $L_6$ from the upper portion thereof (i.e., $L_6=L_4+L_5$). In state A, gas flow control device 90 directs the flow of pressurized gas from the external source, along channel 107, through first shuttle chamber 92A, along channel 104 and into piston chamber housing 31B.

Magnetically biased shuttle valve 93 remains in state A as chamber housing 91B fills with pressurized gas, expanding chamber 3B actively displacing piston 34B away from chamber housing 31B, while causing piston 34A to passively retract back into its piston chamber housing 31A. All the while, inner cannula base 10′″, being operably associated with actuation elements 37A and 37B, undergoes once again a commensurate amount of outwardly directed excursion within cannula cavity 20. With a preselected gas pressure and flow rate set at gas inlet port 100 of device 90, the above-described process of gas filling, venting and flow control occurs automatically at a corresponding rate, resulting in periodic reciprocation of inner cannula 10′″ relative to hand-holdable housing 2. In turn, this periodic reciprocation of inner cannula 4′ results in periodic displacement of the general location of aspiration occurring along the length of the cannula assembly.

Referring to FIGS. 9A through 9F, there is illustrated yet embodiment of the liposuction device of the present invention. In general, liposuction device 1G has a pistol-shaped housing 110 which comprises a barrel portion 111 and a detachable handle portion 112. Instead of using a reciprocating piston motor to translate inner cannula 4′ relative to housing 100, this embodiment utilizes a rotary-type motor 113. In operative association with a cam mechanism, generally indicated by reference numeral 114, rotary-type motor 113 causes actuation element 115 to cyclically slide back and forth and cause inner cannula 4′ to periodically reciprocate relative to barrel portion 111 of the pistol-shaped housing.

As illustrated in FIGS. 9B through 9D, barrel portion 111 of the housing comprises a cannula cavity 116 adapted for slidably receiving cylindrically-shaped base 17 of inner cannula 4′, in a manner described hereinabove. Cannula cavity 116 is also provided with a longitudinally extending access opening, over which a hingedly connected cover panel 117 is provided. As illustrated in FIG. 9E, cover panel 117 facilities insertion of the cannula assembly into, and removal of the cannula assembly from, cannula cavity 116 in a manner similar to that described in connection with liposuction instrument 1A of FIGS. 1A through 1C, in particular. As illustrated in FIG. 9C in greater detail, inner cannula base 10 is adapted to be received within cannula cavity 116 and outer cannula base flange 19 releasably received within annular recess 118 formed in cannula cavity wall 22.

To install inner cannula 4′ into cannula cavity 116, semiflexible transparent tubing 15 is connected to inner cannula outlet port 11. Then cover panel 117 is opened and tubing is fed out through rear port 119 of the barrel portion, as illustrated in FIGS. 9C and 9F. Inner cannula base 10 is then slid into cavity 116 with extensional portion of actuation element 115 received in notch 12. Then outer cannula 5′ is slid over the distal end of inner cannula 4′ until outer cannula base 17 is received within annular recess 118. Thereafter, as shown in FIG. 9E, cover panel 117 is snapped closing using, for example, a spring biased locking device 120, of the type previously described above. Removal of inner and outer cannulas simply involves a reversal of the above procedure.

Alternatively, using spring biased actuation elements and inner and outer cannulas of the type shown in FIGS. 4A and 4B, barrel portion 111 can b e realized without necessity of hinged cover panel 117. In such an alternative embodiment, the inner and outer cannulas can be snap-fitted into and pulled out of cannula cavity 116 in a manner similar to that described hereinabove.

As illustrated in FIGS. 9B through 9F, barrel portion 111 houses cam mechanism 114 which is operably associated with (i) rotary motor 1 13 contained within the handle portion, and (ii) actuation element 115 which slidably passes through a longitudinal slot 121 formed within the upper wall of cannula cavity 116. As in the other previously described embodiments, actuation element 115 includes extension 115A that passes through elongated slot 121 and is received within notch 12 formed in inner cannula base 10. In addition, cam mechanism 114 of the illustrated embodiment inherently embodies gear reduction. In this way, a high angular shaft velocity of rotary motor 113, can be efficiently transformed into reciprocational strokes of the cannula, occurring at a substantially lower rate. With such an arrangement, as rotary motor 113 is caused to rotate under either gas pressure or electrical power, actuation element 115 is caused to reciprocate within elongated slot 121 by way of cam mechanism 114, and thereby cause inner cannula 4' to periodically reciprocate relative to housing 110. This motion results in periodic displacement of the general location of aspiration occurring along the length of the cannula assembly.

As illustrated in FIGS. 9B and 9C, cam mechanism 114 of the preferred embodiment comprises a drive wheel 122 having a first predetermined number of gear teeth 123 disposed thereabout. Drive wheel 122 is rotatably mounted to a shaft 124 mounted through an opening in the top panel of an accommodating section 125 of the barrel portion. Cam mechanism 114 also includes a connective element 126 having first and second ends 126A and 126B, respectively. First end 126A of the connective element is pivotally attached to the drive wheel 122 at a point disposed away from the axial center 124, whereas second end 126B is pivotally connected to actuation element 115 as shown. In order to adjust the distance away from the axis of rotation 124 at which the first end for the connective element is pivotally attached, a radially formed slot 127 is formed in drive wheel 122. Aplurality of widened circular apertures 128 are disposed along radial slot 127 as shown in FIGS. 9B and 9D. In this way, a spring-loaded cylindrical pin 129 passing through the first end of connective element 126, can be selectively locked into one of apertures 128 by pulling upwardly upon pin 129 and setting its cylindrical base 129A into the desired aperture 128. In FIG. 9D, pin 129 is shown to further include pin head 129B, a hollow bore 129B, and an axle 129D having heads 129E and 129F. As shown, a spring 129G is enclosed within bore 129C. about axle 129D and between head 129F and an inner flange 129H. By selectively locking the first end 126A of connective element 126 into a particular circular notch 128 using springloaded pin 129, the distance of the first end of the connective element from axial center 124 can be set, and thus the amount of inner cannula excursion (and effective aspiration aperture displacement) thereby selected. To permit access to spring-loaded pin 129, the top panel of accommodating portion 125 of the housing is provided with a hinged door 132 that can be opened and snapped closed as desired.

As illustrated in FIGS. 9B and 9C, handle portion 112 of the housing encloses a substantial portion of rotary motor 113 whose shaft 133 projects beyond the handle portion and bears a gear wheel 134. As shown, gear wheel 134 has a second predetermined number of gear teeth 134A disposed circumferentially thereabout, which mesh with drive wheel teeth 123. Notably, to permit the rear portion 119 of cannula cavity 116 to extend all the way towards the rear of the barrel portion for passage and exit of aspiration hose 15, shaft 133 of the motor is mounted off center of handle portion 113, as shown in FIGS. 9C and 9F.

Rotary motor 113 is preferably an electric motor whose shaft speed is controllable by the voltage applied to its terminals. Such speed control can be realized by a conventional speed control circuit 135 connected between motor 113 and a conventional 110–115 volt, 50–60 Hertz power supply. As illustrated in FIG. 9C, conventional electrical cord 136 and on/off power switch 150 can be used to connect control circuit 135 and the power supply. Control over the output voltage produced from speed control circuit 115 and provided to electrical motor 113, can be adjusted, for example, by changing the resistance of a potentiometer 137 which is operably connected to the speed control circuit. As shown in FIG. 6C in particular, this potentiometer 137 can be embodied within a trigger mechanism 138 which is connected, for example, to handle portion 112 of housing 110. By pulling trigger 138, the speed of rotary motor 113 can be controlled, and consequently, so too the rate of reciprocation of inner cannula 4' relative to outer cannula 5', and thus the rate of displacement of the effective aspiration apertures.

To connect handle portion 112 to barrel portion 111 and permit disconnection therebetween for cleaning, sterilization and general service, handle portion 112 is provided with flange 140 and thumb-operable spring element 141. Barrel portion 111, on the other hand, is provided with slot 142, catch 143, and cavity 144. To connect handle portion 112 to barrel portion 111, shaft 133 is vertically passed through channels 144 and 145 until gear 134 is slightly below the plane of drive wheel 122. Then, spring element 141 is inserted within cavity 144 while flange 140 is guided into slot 142. By pushing the rear portion of handle 112 in the longitudinal direction of cannula cavity 116, spring element 141 will snap over and clasp catch 143 as shown in FIG. 12C. In this configuration, handle portion 112 is secured to barrel portion 111 and gear teeth 123 will mesh with drive wheel teeth 134A. To disconnect handle portion 112 from barrel portion 11, the surgeon's thumb simply depresses spring-element 141 downwardly and then, by moving handle portion 112 slightly rearwardly, then downwardly, flange 140 is dislodged from slot 142 and motor shaft 133 can be withdrawn from channels 144 and 145. In this disassembled state, handle portion 110 and barrel portion 112 can be individually cleaned and sterilized using conventional procedures known in the surgical instrument art.

Liposuction device 1G described above employed an electric rotary motor to effectuate reciprocation of inner cannula 4' relative to housing 110. However, in an alternative embodiment, it is possible to effect reciprocation of the outer cannula while the inner cannula is stationary with respect to the housing, as shown in FIGS. 6A through 7. Also, it is possible to employ a conventional gas driven rotary motor in lieu of electric rotary motor 113. In such an embodiment, trigger 138 can be operatively associated with a gas flow control valve. Thus, by controlling the rate of gas flow to the gas rotary motor upon actuation of trigger 138, the angular velocity of shaft 133 can be controlled and thus the rate of reciprocation of inner cannula 4' relative to housing 110.

Having described various illustrated embodiments, it is appropriate at this juncture to describe the method of the present invention using, for purposes of illustration only, the liposuction instrument 1C illustrated in FIG. 5.

In general, the surgeon prepares in a conventional manner, the area of skin below which liposuction is to be performed. Typically, this entails marking various zones where radial displacement of the aspiration apertures are to occur. Liposuction instrument 1C of the present invention is assembled as described above so that aspiration apertures 8A', 8B' and 8C' of cannula assembly 3' are in communication with a vacuum source (not shown). A small incision is then made in the patient's skin in a conventional manner, and the distal portion of the cannula assembly is inserted into a premarked radial zone. As pressurized gas is provided to piston motor 6, inner cannula 10 will automatically reciprocate causing the general location of the suction apertures to be automatically displaced along each tunnel of fatty tissue. During the operation of the instrument, the surgeon's hand holding the liposuction instrument is maintained essentially stationary with respect to the patient. Fatty tissue is aspirated through the periodically displaced aspiration apertures, and transferred into a reservoir tank operably associated with the vacuum source.

As deemed necessary, the surgeon can selectively increase the rate of aspiration aperture travel along the distal end of the cannula assembly. This can be achieved by a foot-operated gas flow control device 78 which controls the rate of gas flow to piston motor 6. Also, the amount of inner cannula excursion (i.e., aspiration aperture travel) can also be selected by adjusting the compliance of spring 40 through rotation of threaded element 42.

In the illustrative embodiments described hereinabove, the outer cannula has been made from an electrically non-conductive material (i.e., achieving electrical isolation between the cauterizing electrodes supported on the outer cannula, and electrically conductive inner cannula). The inner cannula has been made from stainless steel, offering the advantage of being easily cleaned and sterilizable. The plastic outer cannula offers the advantage of electrical insulation, low manufacturing cost and disposability. Preferably, when making the outer cannula from a suitable plastic material, injection moulding processes can be used.

In FIG. 10, an alternative embodiment of the liposuction instrument of FIG. 9 is shown. While this embodiment of the liposuction instrument hereof 180 is similar to the embodiment shown in FIG. 9, there are a number of differences. For example, an actuator 181 magnetically-coupled to an air powered cylinder 182 is used to reciprocate the base portion 10 of the inner cannula of its electro-cauterizing cannula assembly. The magnetically-coupled air powered cylinder and actuator subassembly (182, 181) can be realized as Model No. MG 038 commercially available from Tol-O-Matic, Inc. of Hamel, Minn. As shown in FIG. 10, the ends of the air powered cylinder 182 are supported by an external guide and support system comprises brackets 183A and 183B, which are integrated with interior portions of the hand-holdable housing. The actuator block 181, which is mounted about the cylindrical shaft of the cylinder 182, reciprocates between the support brackets 183A and 183B in response to pressurized air (gas) flowing into its first air input/output port 18A, then the second air input/output port 184B, repeatedly in an alternating manner, causing the actuator 181 to reciprocate along the cylinder 182. Such pressurized air streams are provided by an air-flow control device 185.

As shown in FIG. 10A, the air flow control device 185 has one air supply port 185A, first and second air output/return ports 185B and 185C, and first and second air exhaust ports 185D and 185E. Air supply port 185A is supplied with pressurized air through tubing 185A1 connected to flow rate control unit 219 which is controlled by electrical signals produced by trigger 138 when pulled to a particular degree of angular function of deflection. The control unit 219 is to control the flow of air from supply tubing section 219A connected to an external source of pressurized air. The first and second air output/return ports 185B and 185C, are arranged in fluid communication with the first and second air input/output ports 184A and 184B of the cylinder 182, respectively, by way of air tubing sections 186 and 187.

As shown in FIG. 10A, air-flow control device 185 has an air flow control shaft 188 with air flow directing surfaces 188A. Air flow control shaft is slidably supported within the housing of the device. The function of the flow control shaft is to commute air flow between its various ports described above in response to the position of the actuator 181 along the cylinder 182 during device operation. In order to achieve such functions, the air-flow control shaft 188 of the illustrative embodiment is mechanically coupled to an actuator stroke control rod 189 by way of a mechanical linkage 1990. Linkage 190 is supported by brackets 191A, 191B and 191C and secured to the interior of the hand-holdable housing. Along the actuator stroke control rod 189, a pair of actuator stops 192A and 192B are disposed. In the illustrative embodiment, stops 192A and 192B are realized as slidable rods which are adapted to lock into different detented positions along the stroke control rod 189 when the surgeon presses the top thereof (located outside of the housing) downwardly and then in the direction of adjustment, releasing the control stop at its desired location. In some embodiments, it may be desirable to fix one of the control stops while allowing the other control stop to be adjustable along a selected portion of the length of the stroke control rod 189. In alternative embodiments, actuator stroke control can be realized using other types of adjustment mechanisms including, for example, externally accessible adjustment screw mechanism, in which adjustment (rotation) of a single knob or thumb-wheel enables the surgeon to set the stroke length of the inner cannula and thus the aspiration aperture thereof; electronic control mechanisms, in which actuation of an electronic or electrical device, such as foot pad or electrical switch enables the surgeon to translate the position of one or both of the stroke control stops by electro-mechanical means (including linear motors, geared rotary motors and the like.)

Figure 11F:
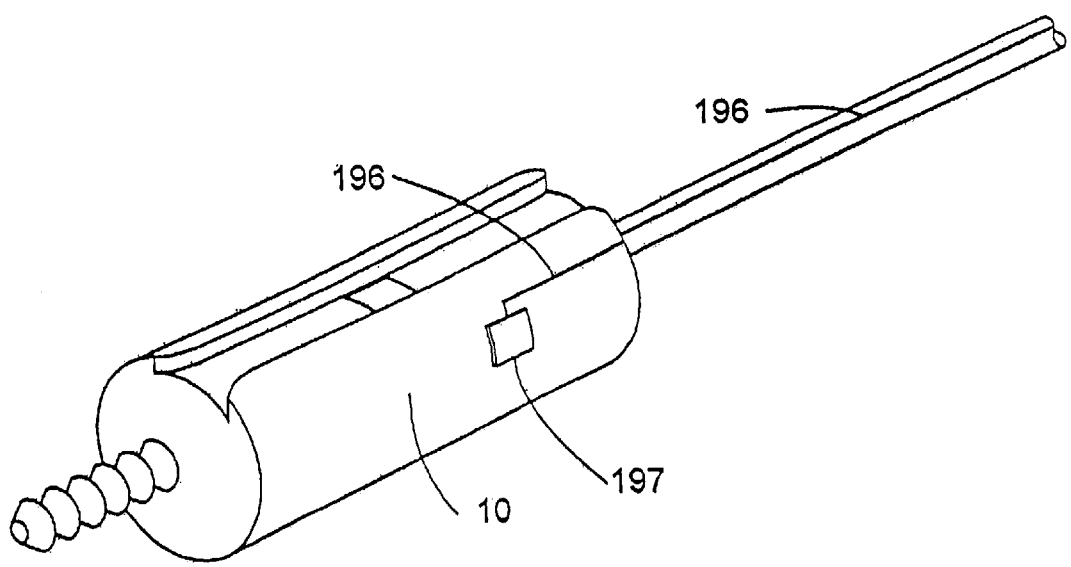
FIG. 11F is a perspective view of the base portion of the electrically-conductive inner cannula shown in FIG. 11 showing an electrical contact pad embedded in the outer surface thereof for conducting the conductive rail embedded in the wall surface of the cannula cavity.

As shown in FIG. 10A, the air flow control shaft 188 has two primary positions; a first position, in which pressurized air from the air supply port 185A is directed to flow through the second air output/return port 188C of the air flow control device, along tubing 187 and into the second input/output port 184B of the cylinder 182, while the second input/outlet port 184B of the cylinder is in communication with the first exhaust port 185D of the air flow control device 185 causing inner cannula to project away from the housing; and a second position, in which pressurized air from the air supply port 185A is directed to flow through the first air output/return port 188B of the air flow control device, along tubing 186 and into the first input/output port 184A of the cylinder, while the second input/outlet port 184B of the cylinder is in communication with the second exhaust port 185E of the air flow control device 185, causing the inner cannula to retract inwards towards the housing. By virtue of this arrangement, the actuator 181 is automatically driven back and forth between stroke control stops 192A and 192B along the cylinder stroke rod in response to pressurized air flow into the air flow control device 185. When the electro-cauterizing cannula assembly of FIG. 11A is installed within the cannula cavity of the liposuction device, as described hereinabove, the inner cannula 4 will be caused to reciprocate relative to the outer cannula 5. In the illustrative embodiment, the length of the excursion of the inner cannula 4 is determined by the physical spacing between mechanical stops 192A and 192B. By varying the spacing of these stops along the stroke control rod 182, the maximum excursion of the inner cannula relative to the stationary outer cannula can be simply and easily set and reset as necessary by the surgeon.

In FIG. 11A, an electro-cauterizing cannula assembly 3″ is shown for use with the liposuction instrument of FIG. 10. In this illustrative embodiment, both the inner and outer cannulas are made of an electrically non-conductive material such a sterilizable plastic. In the embodiment of FIG. 10, hand-holdable housing is preferably made from an electrically non-conductive material. Electrically conductive electrodes 195A, 195B, 195C and 195D are inserted within the inner aspiration apertures 8A, 8B, 8C and 8D and electrical wiring 196 run to the inner cannula base portion 10, wherein an electrical contact pad 197 is embedded. Electrically conductive electrodes 160A, 160B, 160C and 160D are also inserted within the outer aspiration apertures 16A, 16B, 16C and 16D, and electrical wiring 168 run to the outer cannula base portion 19, wherein an electrical contact pad 166B is embedded. An electrical contact pad 176B is also embedded within the base portion recess within the hand-holdable housing.

Figure 11G:
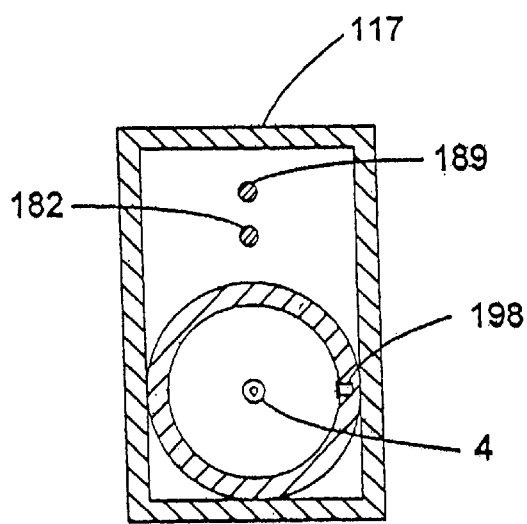
FIG. 11G is a cross-sectional view of the liposuction instrument taken along line 11G—11G of FIG. 10.

As shown in FIGS. 10 and 11, an electrical contact rail 198 is embedded within the side wall surface of the cannula cavity so that electrical contact pad 197 or base portion 10 of the inner cannula establishes electrical contact therewith to apply RF (supply/return) power signals to the electrodes in the inner cannula during liposuction operations. In such circumstances, two sets of electrical connections occur. Firstly, the base portion 10 of the inner cannula is securely engaged by the actuator block 181 (snap-fitting or other suitable means) and the electrical contact pad 197 contact with the electrical rail 198 embedded within the inner side wall surface of the cannula cavity. Secondly, the base portion 19 of the outer cannula is received within the base portion recess of the hand-holdable housing and the electrical contact pad (i.e., RF power supply terminal) 176B embedded therewithin establishes contact with the electrical contact 166B embedded within the base portion of the outer cannula. By virtue of these electrical connections, RF supply potentials are applied to the electrode portions of the inner cannula, while RF return potentials are applied to the electrode portions of the outer cannula, whereby electro-cauterization occurs.

In FIG. 13A through 13D, an alternative electro-cauterizing cannula assembly 3′″ is shown for use with the liposuction instrument shown in FIGS. 10 and 10A, and readily adaptable for use with other liposuction instruments of the present invention. In this particular illustrative embodiment, both the inner and outer cannulas are made of an electrically conductive material. The hand-holdable housing is made from an electrically non-conductive material (e.g., plastic). Between these electrically conductive cannulas 4 and 5 means are provided for maintaining electrical isolation between the electrically conductive carrier and outer cannula which, during electro-cauterization, are maintained at an electrical potential difference (i.e., voltage) of 800 volts or more. In general, a variety of different techniques can be employed for carrying out this functionality. For example, a thin coating of Teflon® material 200 can be applied to the outer surface of the outer cannula. Alternatively, a series of electrically-insulating spacer/washers made from Teflon® ceramic, or like material can be mounted within circumferentially extending grooves formed periodically about the inner cannula to maintain sufficient spacing and thus electrical insulation between the inner and outer cannulas. Preferably, the spacing between each pair of insulating spacers is smaller than the length of the bore 18 formed in the electrically conductive base portion of the outer cannula , as illustrated in FIG. 13A.

The electrical contact rail (i.e., RF power supply terminal) 198 embedded within the cannula cavity establishes electrical contact with the base portion of the inner cannula when the cannula assembly is installed in the housing of the device. Also, electrical contact pad 176B embedded within the recess portion of the housing establishes electrical contact with the base portion of the outer cannula when the cannula assembly is installed within the hand-holdable housing. In the assembled state, two sets of electrical connections occur. Firstly, the electrically conductive base portion of the inner cannula is engaged by the electrical contact rail 198. Secondly, the base portion of the outer cannula is received within the base portion recess and the base portion of the outer cannula establishes contact with the electrical contact 176B embedded within the recess portion. By virtue of these electrical connection, RF supply potentials are applied to the inner cannula, while RF return potentials are applied to the outer cannula. The potential difference(s) between these surfaces about the aspiration apertures enable electro-cauterization of tissue as it is being aspirated through the aspiration aperture moving along the cannula assembly.

In another illustrative embodiment of the present invention, the inner cannula 4 is made of an electrically non-conductive material such as plastic. The outer cannula is made of electrically conductive material (e.g., stainless steel). The hand-holdable housing is made from an electrically non-conductive material (e.g., plastic). Electrically conductive electrodes are inserted within the inner aspiration apertures thereof, and electrical wiring run to the inner cannula base portion, wherein an electrical contact rail is also embedded.

Figure 14E:
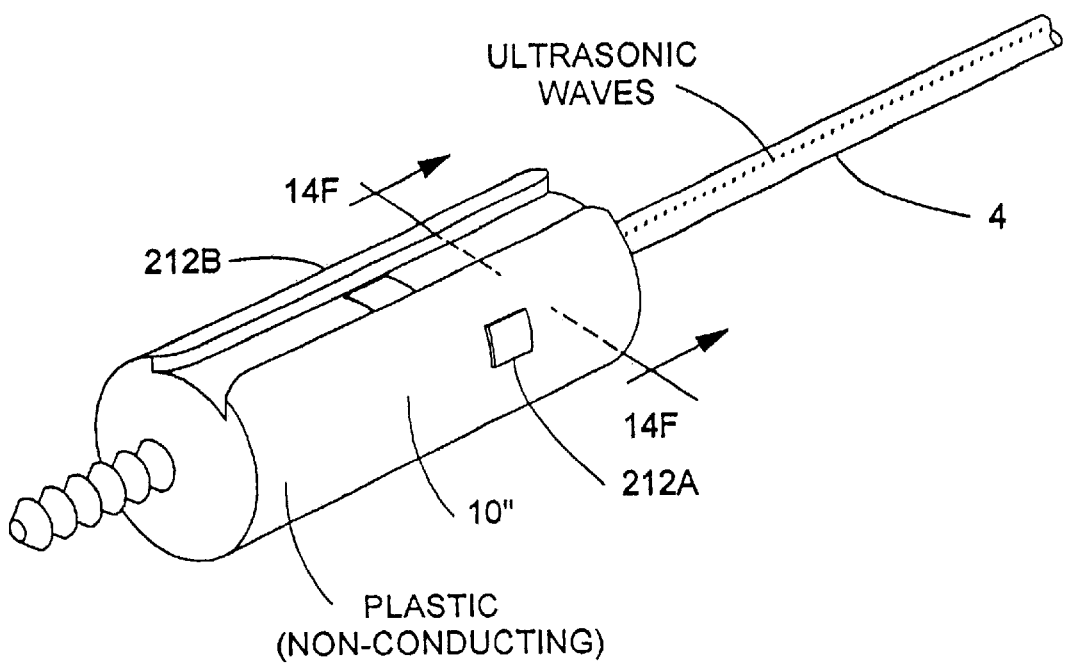
FIG. 14E is a prospective view of the base portion of the inner cannula used in the cannula assembly of FIG. 14B, wherein an electrical contact pad is embedded in the side wall surface thereof of the base portion for engagement with an electrically conductive rail embedded within the side wall surface of the cannula cavity within the liposuction instrument of FIG. 14.
Figure 14F:
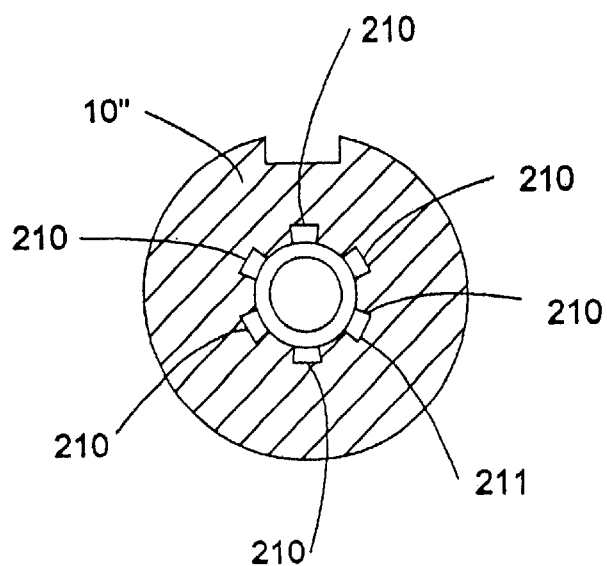
FIG. 14F is a cross sectional view of the base portion of the inner cannula taken along line 14F—14F in FIG. 14E, showing a plurality of piezo-electrical transducers arranged about the lumen of the inner cannula for producing and conducting ultrasonic energy signals for propagation along the length of the inner cannula.
Figure 14G:
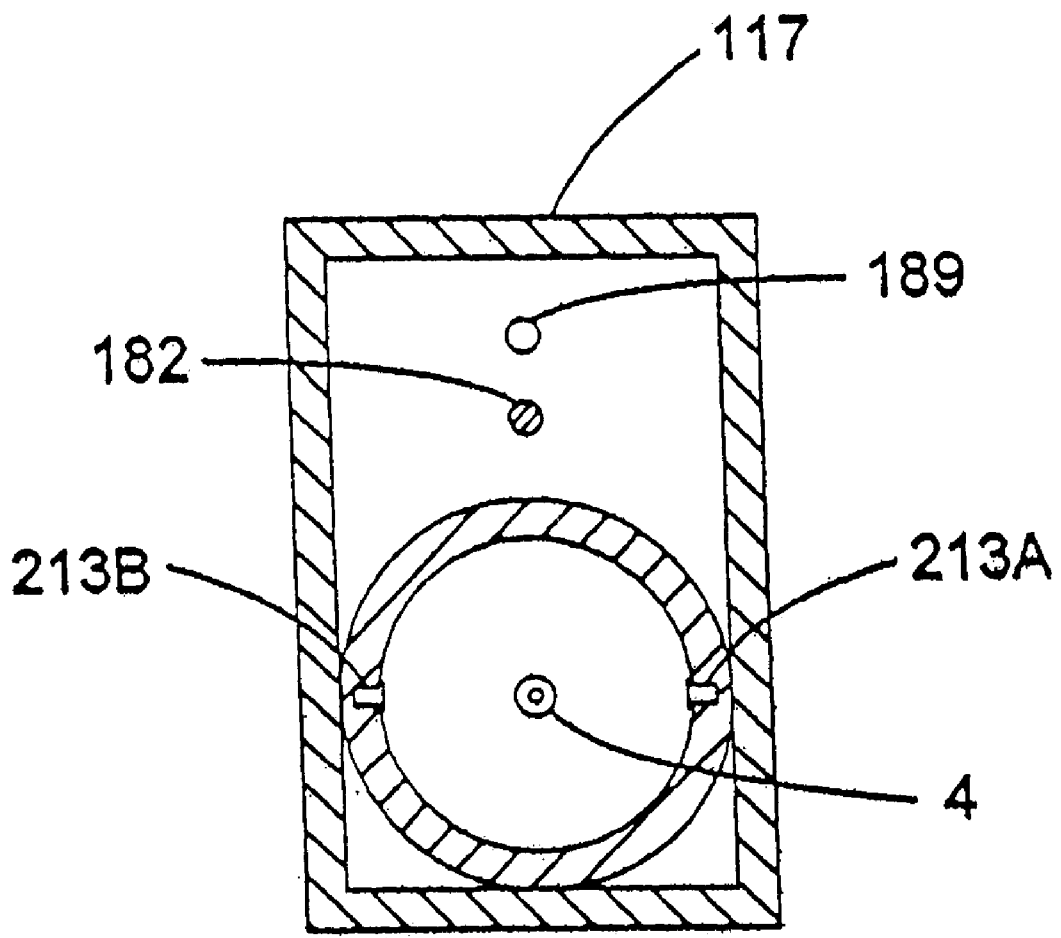
FIG. 14G is a cross sectional view of the liposuction instrument of FIG. 14 taken along line 14G—14G of FIG. 14, showing a pair of diametrically opposed electrically conductive rails embedded within the interior wall surfaces of the cannula cavity of the liposuction instrument, which establish electrical contact with a pair of electrical contact pads embedded within the base portion of the inner cannula and are connected to the array piezo-electric transducers mounted about the outer lumen of the inner cannula.
Figure 15:
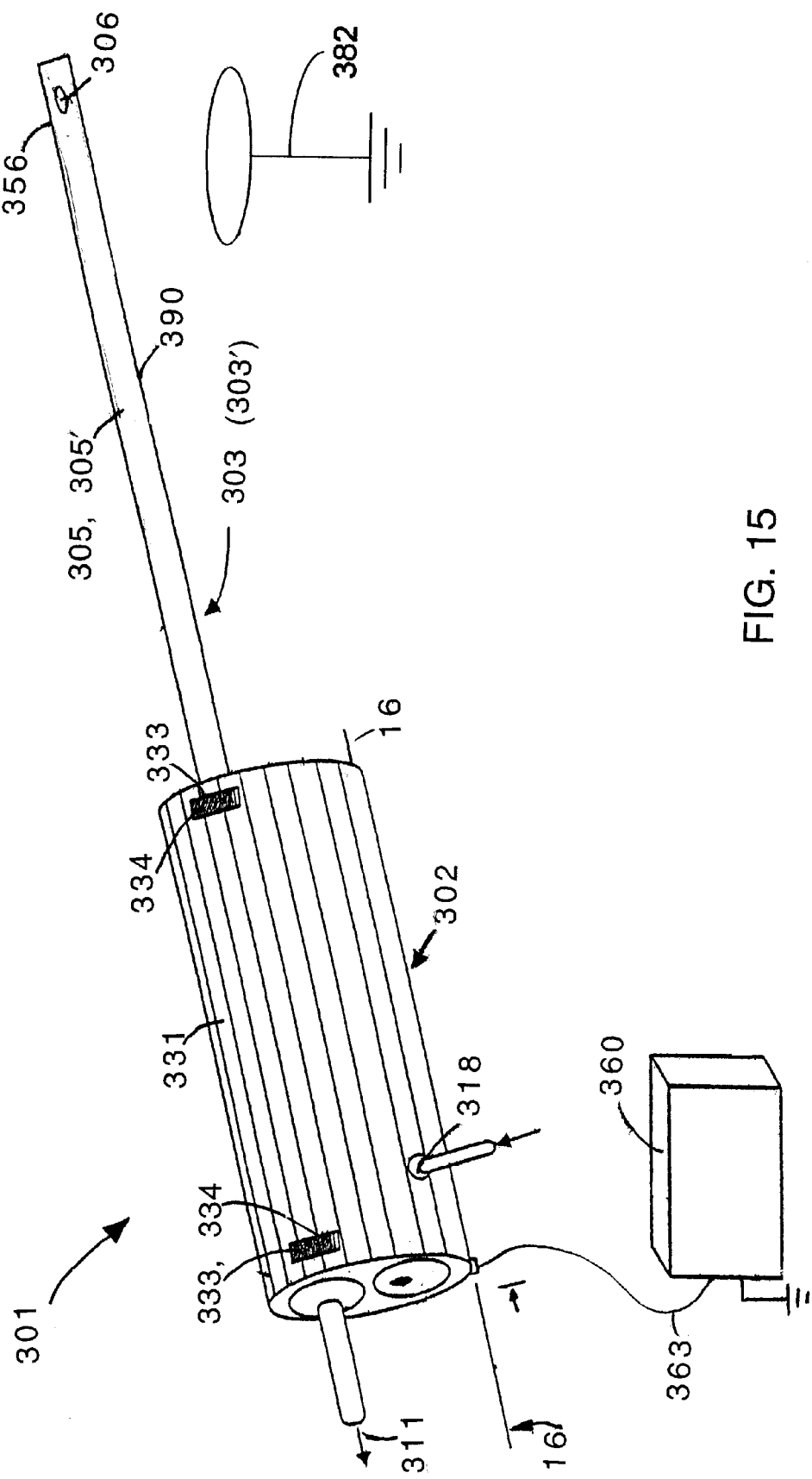
FIG. 15 is a perspective view of another embodiment of the liposuction device of the present invention provided with monopolar electrocautery electrode structures along the distal portion of a single cannula assembly.

As shown in FIG. 14G, an electrical contact rail 213A is also embedded within the side wall of the cannula cavity. An electrical contact pad embedded within the recess of the plastic hand-holdable housing establishes electrical contact with the base portion of the electrically conductive outer cannula. Thus, when the cannula assembly is installed within the hand-holdable housing, two sets of electrical connections occur. Firstly, the base portion of the inner cannula is engaged by the actuation means and the electrical contact p ad therewithin establish contact with the electrical contact embedded within the base portion of the outer cannula. By virtue of these electrical connections, RF supply potential are applied to the electrode portions of the inner cannula, while RF return potentials are applied to the electrode portions of the outer cannula.

In yet other alternative embodiments of the present invention, hemostasis can be carried out in the powered liposuction instruments hereof by producing ultrasonic energy (having a frequency of about 50 kilohertz) and delivering the same to the aspiration aperture regions of the cannula assembly during liposuction procedures. Such ultrasonic energy will cause protein coagulation of aspirated tissue in the regions of the aspiration apertures. When the frequency of the ultrasonic energy is reduced to about 20–25 kilohertz, liquefaction or lipolysis of the aspirated tissue will occur. Such modes of operation can be added to any of the electro-cauterizing liposuction instruments of the present invention, or to liposuction instruments with electro-cauterizing capabilities.

In FIGS. 14 through 14C, a preferred embodiment of the ultrasonic cauterizing liposuction instrument of the present invention is shown. In general, the embodiment shown in FIGS. 14 through 14C is similar to the liposuction instrument of FIG. 10, except that it includes several additional means which enable it to effect protein coagulation (and thus hemostasis) during liposuction using ultrasonic energy having a frequency of about 50 kilohertz and sufficient power. As shown, a set of piezo-electric crystals 210 are embedded about the lumen of the inner cannula and encased within the base portion of the inner cannula made of plastic.

As shown in FIG. 14, an electrical signal generator 216 external to the liposuction device is provided for supplying electrical drive signals to terminals 214 via control circuit 215 when it is enabled by manual actuation of trigger 138. The electrical signal generator 216 should be capable of producing electrical signals having a frequency in the range of about 15 to 60 kHz, at a sufficient power level. Any commercially available signal generator, used in medical applications, can be used to realize this system component. The electrical signals produced from generator 216 are applied to the terminals of the piezo-electric transducers embedded within the electrically non-conductive base portion of the inner cannula.

When the generator 216 is switched to produce signals in range centered about 20 kHz, these signals are delivered to the array of piezo-electric transducers embedded within the base portion of the inner cannula. These drive signals cause the piezo-electric transducers to produce ultrasonic signals in substantially the same frequency range to propagate along the surface of the inner cannula and out the inner and outer aspiration apertures, enabling lipolysis or liquefaction of aspirated fat tissue.

When the generator is switched to produce signals in range centered about 50 kHz, these signals are delivered to the array of piezo-electric transducers embedded within the base portion of the inner cannula. These drive signals cause the piezo-electric transducers to produce ultrasonic signals in substantially the same frequency range to establish standing waves within the inner cannula which propagate out the apertures of inner and outer cannula, enabling coagulation of protein molecules within aspirated tissue, thus achieve hemostasis.

While carrying out lipolysis using ultrasonic energy producing means within the liposuction device hereof, the surgeon may also desire to conduct hemostasis by coagulating protein molecules within tissue being aspirated. As shown in FIG. 14, by pulling trigger 138, control circuit 217 automatically commutes RF supply and return signals from the RF signal supply unit 175 to power supply terminals 218 which, in turn, are connected to contact pads 176A and 176B embedded within recess 17A, supporting the base portion of the outer cannula with respect to the hand-holdable housing.

As shown in FIGS. 10 and 14, a flow control switch 219 is provided within the handle of the housing in order to enable the flow of pressurized air from air supply to the reciprocation means (e.g., cylinder 182, etc.) only when manually actuated trigger 138 is manually actuated (or a foot pedal is depressed). When the trigger 138 is pulled, an electrical signal is sent to the flow control switch 219 which, in turn, permits a selected amount of pressurized air to flow into the reciprocation device (e.g., cylinder 182). The trigger switch 138 can have a number of positions, at which different electrical signals are produced for enabling flow control switch 219 to allow pressured air to flow to the reciprocation means 182 at different flow rates. This can be used to control the rate of reciprocation of the inner cannula relative to the outer cannula, providing the surgeon with additional control over the tissue aspiration process.

Notably, an improved degree of surgical control and user safety are provided by the liposuction instrument of the present invention described above.

In particular, control circuit 217 prevents the liposuction instrument hereof from carrying out cauterization along the length of its cannula assembly, unless the cannula is reciprocating and/or aspirating. This condition is detected when the trigger 138 is pulled to a particular degree of angular deflection. The reason for providing such control over the electro-cauterization functionality of the liposuction device hereof is to prevent inadvertent burning of tissue during liposuction and like procedures.

The function of the control logic circuit 215 is to enable the commutation of 20–25 kilohertz electrical signals between the generator 216 and the power supply rails 213A and 213B (to energize the piezo-electric transducers 210 in the base portion of the inner cannula) only when aspirated tissue is flowing through the inner cannula. This condition is detected when the trigger 138 is pulled to a particular degree of angular deflection.

The electro-cauterization electrodes of the liposuction devices hereof can be controlled in a variety of different ways. One way would be to continuously enable RF-based electro-cauterization during sensed tissue aspiration. In such "continuously-enabled" embodiments of the present invention, there will typically be no need for external switches to activate the electro-cauterizing electrodes embodied within the cannula assembly of the present invention.

Another way would be to enable RF-based electro-cauterization by way of switching RF supply and return signals to the electrodes during sensed tissue aspiration and supply of an activation signal by the surgeon. Generation of the activation signal can be realized by manually actuating a second trigger, or pushing a button, or depressing a foot pedal, external to the hand-supportable housing, or by automatically detecting a particular condition along the aspiration channel of the device or elsewhere therein.

While the liposuction instruments described above have been shown to include four symmetrically arranged aspiration apertures, it may be desired in particular applications to provide a cannula assembly having inner and outer cannulas with one, two or three aspiration apertures, rather than four as shown in the illustrative embodiments.

In some applications it may be desired to provide a cannula assembly having a pair of diametrically opposed aspiration apertures, and an outer cannula with a single aspiration aperture. The outer cannula assembly can be adapted to be rotatable in one of two angular positions about the inner cannula. In the first position, the single aspiration aperture formed in the outer cannula is aligned in registration with the first aspiration aperture along the inner cannula. When rotated into its second angular position, the single aspiration aperture of the outer cannula is aligned in registration with the second aspiration aperture along the inner cannula. The surgeon can easily switch the outer cannula between its first and second angular positions by rotating a small radially extending projection, adjacent the hand-holdable housing, in either a clockwise or counter-clockwise direction to align the aspiration aperture on the outer cannula in registration with the selected aspiration aperture on the inner cannula. This feature of the present invention provides the surgeon with the option of changing which side of the distal end of the cannula assembly is enabled to aspirate tissue during a liposuction procedure without the necessity of removing, repositioning and reinserting the cannula assembly within the housing. This technical feature can be used in conjunction with both electro-cauterizing as well as ultrasonic cauterizing functionalities of the present invention described above. When this aspiration aperture orientation control feature is provided in a liposuction instrument of the present invention having cauterizing electrodes embedded about the aspiration aperture(s) of a plastic outer cannula, an electrical communication mechanism can be embodied within the outer cannula the proximal portion thereof and its base portion so that electrical connectivity can be achieved between the cauterizing electrode on the outer cannula and its electrically conductive contact pad embedded within the base portion of the outer cannula.

As shown in FIGS. 15 through 19, the liposuction device of the present invention may be equipped with a monopolar-type electro-cauterizing cannula assembly, in contrast with the bipolar designs shown and described in detail hereinabove. While the monopolar-type liposuction instrument of the present invention is shown embodied within the general design of FIGS. 1A through 1C, with appropriate modifications, it is understood that any of the alternative embodiments shown and described hereinabove can be readily modified to provide a monopolar-type electrocauterizing cannula assembly in accordance with the principles of the present invention As illustrated in greater detail in FIGS. 15 and 16, the liposuction device 301 comprises an hand-holdable housing 302, a detachable cannula 303 with a monopolar electro-cauterizing electrode(s), and a reciprocation mechanism 304 for causing the cannula 303 to reciprocate relative to the housing. Cannula 303 of the present invention comprises an elongated tube 390 having an aspiration (i.e. suction) aperture 306 at its distal end and a base 307 operably associated with the proximal end of the tube 390. Preferably, cannula base 307 has an outlet port 308 formed at its remote end, and a notch or recess like structure 309 formed in its central most portion, as shown. As will be described in greater detail hereinafter, notch structure 309 functions to releasably receive a terminal portion of the electrically-conductive actuator element 312, in order to engage therewith and thereby actuate reciprocation of cannula 303 within housing 302 during operation of the reciprocation mechanism 304. In alternative embodiments of the present invention, the notch like structure 309 can be realized in variety of different ways depending, of course, on the structure of the actuator 312.

Figure 16:
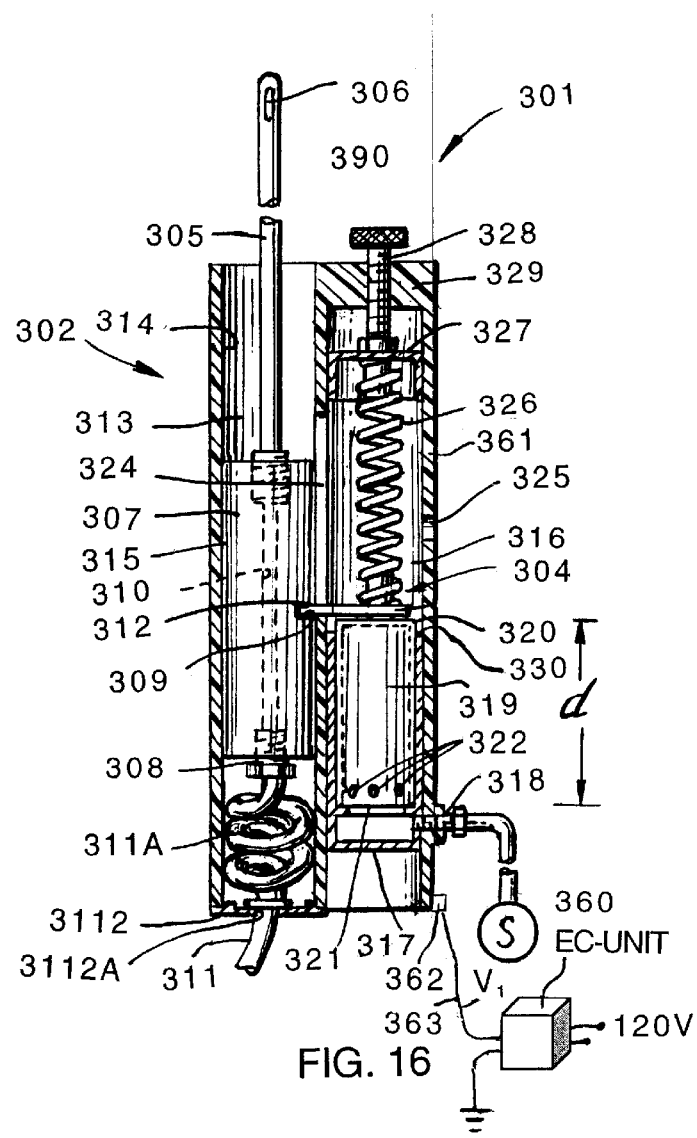
FIG. 16 is a cross-sectional view of the liposuction device of the present invention taken along line 16—16 of FIG. 15.
Figure 19:
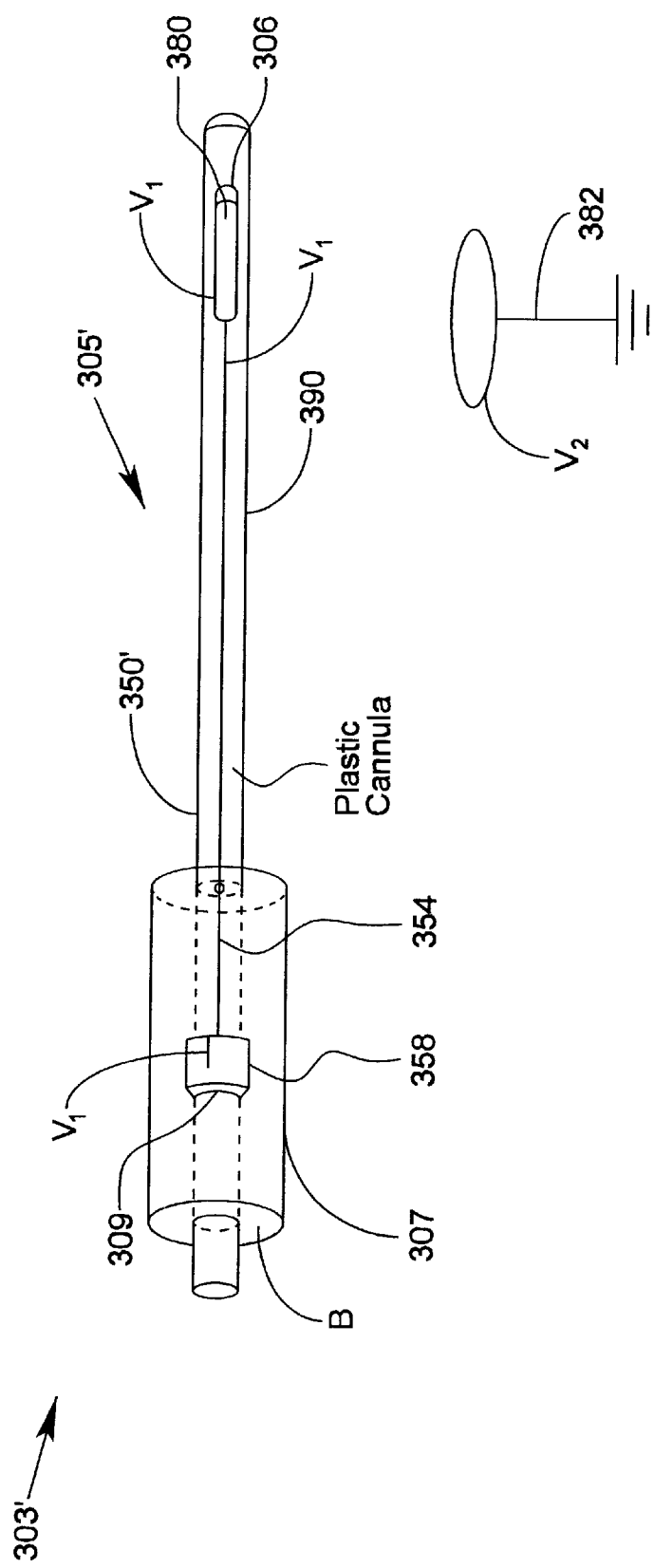
FIG. 19 is a perspective view of a second illustrative embodiment of the monopolar electro-cauterizing cannula assembly of the present invention shown removed from the hand-supportable device of FIG. 15, wherein an electrically-conductive cauterizing electrode, in the form of an eyelet-like structure, is mounted about the perimeter of the aspiration (i.e. suction) aperture in the cannula assembly, and electrically connected to the active lead of a unipolar electro-cautery power supply unit when the cannula assembly is installed within the hand-supportable device and the device is electrically connected to the power supply unit by way of any electrical cable.

As shown in FIGS. 16, 18 and 19, the shape of cannula base 307 is preferably cylindrical and will match the bearing surfaces which guide the cannula as it is caused to reciprocate within housing 302. As illustrated, cannula 303 (303') has a continuous passageway 310 which extends from aspiration aperture 306 to outlet port 308 for transporting aspirated fat tissue through aperture 306 to a conventional vacuum source (not shown). To achieve this function, the vacuum source is connected to outlet port 308 using preferably optically transparent, semi-flexible tubing 311.

As shown, the gross geometry of the housing 302 is preferably that of an ellipsoid, however, other geometries such as, for example, as a cylindrical structure, can be used in practicing the present invention. Housing 302 has a cannula cavity generally indicated by reference numeral 313, and has generally cylindrical bearing surfaces 314 which match the outer bearing surface 315 of cannula 303, to permit sliding movement of cannula 303 within 313. While cylindrical bearing surfaces have been selected in the preferred embodiment, use of other forms of bearing surfaces (e.g., rectangular or triangular) are contemplated. To minimize friction, bearing surfaces 314 and 315 may be coated with a Teflon® or functionally equivalent coating, to facilitate easy sliding of cannula base 307 within cavity 313 with low wear.

Figure 17:
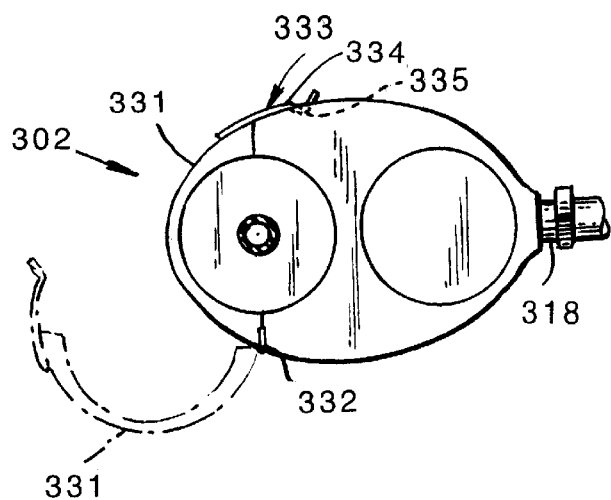
FIG. 17 is an elevated end view of the liposuction device of the present invention illustrated in FIG. 15, showing the monopolar electro-cauterizing cannula assembly thereof retained within the cannula cavity of its hand-holdable housing, and with the hingedly connected housing cover panel disposed in a n open position for removal of the cannula assembly therefrom.

As illustrated in FIG. 17, housing 302 of the illustrative embodiment is provided with a hinged cover 331. Hinged cover 331 allows cannula cavity 313 to be opened and accessed and cannula 303 to be selectively installed in and removed from housing cavity 313. Cover panel 331 has a semi-circular cross-sectional geometry and is connected to the remainder portion of the housing 302 by a conventional hinge means 332. To secure cover panel 331 to the remainder of housing 302, a releasable locking means 333 is provided at the interface of hinge cover 331 and the remainder portion of housing 302, as shown. Releasable locking means 333 can be realized in a variety of ways, including, for example, using a spring biased clamp element 334 which engages in a notch 335 formed in the external surface of the remainder portion of the housing 302, as illustrated in FIG. 17.

In the case of the cannula assembly design of the first illustrative embodiment shown in FIG. 18, the distal and proximal portions of the cannula 303 are made from an electrically conductive lumen material 350 having a non-conductive coating 352 (e.g. made from TFE coating or outer plastic sheath) applied thereover. Preferably, the non-conductive coating 352 disposed upon or applied over the electrically-conductive cannula 303 forms a cauterizing electrode 356 about on the inner edge walls of the aspiration aperture 306, as shown in FIG. 18.

The function of the aspiration aperture 306 is to ensure that aspirated fatty tissue is subject to an electrical potential difference (i.e. V1–V2) maintained between the cauterizing electrode and reference ground, which is sufficient to electro-cauterize fatty tissue as the same is being aspirated through the aspiration aperture. In this illustrative embodiment, the electro-cauterizing electrode 356 formed about the outer edge of the aspiration aperture 306 is maintained at electrical potential V1 by way of a first electrically conductive pathway realized along the cannula assembly, best illustrated in FIGS. 18, 18A and 18B. As shown in these drawings, electrical contact plate 358 can be embedded within the notch 309 formed in the base portion 307 of the cannula assembly, while an electrically conductive post 354 affixed to contact plate 358 establishes electrical contact with the distal portion of the electrically conductive lumen 350. By virtue of the fact that the electro-cauterizing electrode 356 is realized from the conductive material of the electrically conductive lumen 350, which is in electrical contact with the electrical contact plate 358 via electrically-conductive post 354.

In the case of the cannula assembly design of FIG. 19, the cannula 303' is made from an electrically non-conductive material (e.g. plastic) having an electro-cauterizing electrode 380 (realized in the form of any eyelet or like structure) mounted about each cannula aspiration aperture 306 provided at the distal end of the cannula. As will be described in greater detail below, preferably the electrode 380 is formed on the inner edge wall of the aspiration aperture and is maintained at electrical potential V1 whereas the human patient is maintained at electrical ground potential V2=0 Volts, so that, during liposuction procedures, aspirated fatty tissue is subject to a potential difference (i.e. V1–V2), sufficient to electro-cauterize the fatty tissue as it is being aspirated through the aspiration aperture 306. As shown in FIG. 19, the same or modified electrical contact plate 358 of FIG. 18A can be embedded within the notch 309 formed in the base portion 307 of the cannula assembly 305'. As shown, the base portion of the electrically conductive post 354 is maintained in electrical contact with the electro-cauterizing electrode 380 by an electrical wire 354, embedded within the outer surface of the electrically non-conductive lumen 350', and electrically connected thereto so as to maintain these structures at the same electrical potential.

As shown in FIG. 16 when either cannula assembly 305 or 305' is properly loaded within the hand-supportable housing 302 of the liposuction instrument of the present invention, the electrically-conductive actuator 312 engages with the electrical contact plate 358 in notch 309 of the cannula base portion. In order to maintain the electro-cauterizing electrode(s) provided along the distal portion of the cannula assembly (305 or 305'), electrical contact plate 358, to which the electro-cauterizing electrodes are connected, must be electrically connected to the output lead of a unipolar cautery unit 3 60 -which generates a radio-frequency (RF) power signal maintained at voltage potential V1, referenced to electrical ground, V2, which is zero volts. This electrical connection between the cautery unit 360 and embedded electrical contact 358 in the base portion of the cannula assembly (305 or 305') can be established using internal wiring 361 which extends from electrically-conductive spring support plate 327 and power jack 362 mounted within the wall of the housing. Such internal electrical wiring can be embedded within the walls of hand-supportable housing 302 or otherwise routed within the same. Notably, the actuator 312, spring 326 and spring support plate 327 are each made from an electrically conductive material so as to each be maintained at substantially the same electrical potential.

As shown in FIG. 16, a flexible shielded-type power cable 363 is used to electrically connect the power jack 362 on the liposuction instrument to the output power lead of the electro-cautery power supply unit 360. By way of this arrangement, the electro-cauterizing electrode 356 in the cannula assembly (305 or 305') is maintained at a relatively high electrical voltage V1, while the tissue of the patient to be aspirated is maintained at a substantially lower voltage V2 by virtue of grounding plates attached to the patient during a liposuction procedure conducted in accordance with the principles of the present invention.

In alternative embodiments of the present invention, the hand-supportable housing may not be provided with a hingedly connected cover panel, as shown in FIG. 17, but rather the base portion of the cannula can be adapted to slide into the cannula cavity 313 and snap-fit into the actuator 312 which may be realized using a spring-loaded ball or like structure, as taught in Applicant's U.S. Pat. No. 5,112,302, incorporated herein by reference in its entirety. In other embodiments, the base portion of the cannula assembly and the actuator associated with the reciprocation mechanism may be realized in virtually any manner than enables slidable movement of the cannula relative to the hand-supportable housing, and supply of the electrical voltage VI to the electro-cauterizing electrode associated with the cannula, regardless of whether the electro-cauterizing electrode is realized using the methods illustrated in FIGS. 16, 18 and 19, or by any other means.

In general, a gas, air or electrically driven motor(s) can be used to realize the reciprocation mechanism 304 of present invention and thus effectuate reciprocation of cannula 303 within cannula cavity 313. In the embodiments illustrated in FIGS. 15 through 19, a gas driven piston-type motor is employed, although it is understood, that other type of motor, including rotary and linear motors alike, can be used to the realize reciprocation mechanism 304 of the liposuction instrument of the present invention.

As illustrated in FIG. 16, a piston-type motor 304 is mounted within a motor cavity 316 provided adjacent cannula cavity 313 of housing 302. In general, motor 304 comprises a chamber housing 317 having a gas inlet port 318 and an inner chamber generally indicated by reference numeral 319. Slidably received within the inner chamber of housing 317 is a movable piston 320 having formed in its lowermost wall 321, one or more gas outlet ports 322. Mounted to the top portion of movable piston 320, is actuation element 323 which projects through a longitudinally disposed slot 324 formed in the bearing wall 314 of cannula cavity 313. Projection 312 of actuation element 323 through the slot 324, is received within notch 309 formed in cannula base 307 and operably associates cannula 303 with motor 304.

As illustrated in FIG. 16, chamber housing 317 is fixedly disposed within motor cavity 316. Motor cavity 316 is also provided with at least one port 325 for ventilating to the ambient environment, gas released from movable piston 320 upon reaching it maximum displacement or excursion. Movable piston 320 is biased in the direction of chamber housing 317 by way of a spring biasing element 326. The compliance of spring biasing element 326 can be adjusted by moving the position of slidable wall 327 by rotating, for example, threaded element 328 passing through a portion 329 of the housing 302, as shown. With this arrangement, adjustment of wall 327, closer to or farther from chamber housing 317, results in decreasing or increasing, respectively, the compliance of spring biasing means 326. This, in turn, provides a simple, yet reliable way in which to control the rate of reciprocation of movable piston 320, and thus the rate of reciprocation of cannula 303 relative to housing 302.

The manner of operation of piston-type motor 304 is described as follow. Gas, such as pressurized air of $N_2$ gas, is introduced under constant pressure to inlet port 318 of chamber housing 317. As the gas fills up the volume enclosed by the interior walls of the movable piston and the chamber, inner chamber 319 begins to expand, forcing movable piston 320 upwardly against the biasing force of spring biasing element 326. When movable piston 320 is displaced sufficiently enough from chamber housing 317 so that gas within expanding chamber 319 can be released through gas exit port 325 to the ambient atmosphere, piston 320 will be forced back downwardly into chamber housing 317 at a rate inversely proportional to the compliance of spring biasing element 326. Subsequently, chamber 319 will again fill up with gas, piston 320 will again be displaced and gas subsequently vented, whereupon reciprocating displacement of piston 320 will be repeated again in a cyclical manner. Since movable piston 320 is operably connected with cannula base 307 by way of actuation element 323, this reciprocating movement of piston 320 results in reciprocating movement of cannula 303 within cannula cavity 313.

As illustrated in FIG. 16, the amount of excursion that the piston is permitted to undergo before gas venting and subsequent downward piston movement occurs, is determined by the distance "d" defined gas output port 322 and top wall surface 330 of chamber housing 317. Typically, a cannula excursion distance of three inches, for example, will necessitate that the parameter d, defined above, also be about three inches.

To use the liposuction device 301 of the illustrative embodiment described above with either cannula assembly 305 or 305', the surgeon inserts either the cannula assembly shown in FIG. 18 or 19 into the cannula cavity of the hand-supportable housing 302 so that the actuator 312, or other embodiment thereof, engages within the notch 309 or like structure within the base portion of the cannula assembly, and secures the cannula assembly within the hand-supportable housing, as shown, for example in FIG. 16. A grounding plate or strap 382 is applied to the skin of the patient in a conventional manner, and the grounding strap is then connected to the V2 terminal of the electro-cautery power supply unit 360. The surgeon then activates the air power supply to the instrument, as well as the electro-cautery power supply unit 360. Then, while holding the housing within the grasp of the surgeon's hand, the surgeon performs a liposuction procedure in a normal manner. During the procedure, the instrument effectuates periodic displacement of the general location of aspiration along the distal end of the cannula assembly, through the reciprocating movement of cannula while permitting electro-cauterization of aspirated tissue during operation of the liposuction device.

When performing a liposuction procedure using the cannula assembly shown in FIG. 18, the tissue of the patient to be aspirated through the aspiration aperture 356 is maintained at electrical ground potential by way the grounding plate 382. At the same time, the electro-cauterizing electrode 356 is maintained in electrical contact with the active output terminal of the unipolar cautery power unit 360 by virtue of the of electrical pathway established therebetween and described in detail above. It is understood, however, that there are a variety of different electrical paths that may be established to maintain the electro-cauterizing electrode(s) 356 in electrical contact with the output power terminal of the unipolar cautery power unit 360. Thus, during a liposuction procedure, the sample of tissue about to be aspirated through the aspiration aperture is maintained at a difference in electrical potential (i.e. at a voltage) equal to the electrical potential of the active output power terminal $V_2$, referenced to zero volts ground potential $V_1$. In practice, t his voltage is sufficient to electro-cauterize tissue during aspiration to prevent hemorrhaging and the like to the patient, thereby improving the safety of the procedure.

The above-described mono-polar electro-cauterizing liposuction instrument can be modified in many ways. For example, the form factor of the hand-supportable housing may be realized in the form of the other hand-supportable housing shown herein. Also, the means and way by which the electro-cauterizing cannula assembly physically and electrically connects to the actuator and thus the reciprocation mechanism within the hand-supportable housing may vary from embodiment to embodiment of the present invention.

While the particular embodiments shown and described above have proven to be useful in many applications in the liposuction art, further modifications of the present invention disclosed herein will occur to persons skilled in the art to which the present invention pertains. All such modifications are deemed to be within the scope and spirit of the present invention defined by the appended claims.

What is claimed is:

1. Apparatus for use in liposuction treatment of tissue on a patient operably connected to an electrical grounding plate, which comprises:

a hand-holdable housing having a longitudinal axis;

a reciprocation mechanism disposed within said hand-supportable housing;

a hollow cannula operably connectable to said hand-holdable housing and said reciprocation mechanism and having a distal end, a proximal end, and a suction aperture disposed about said distal end, said proximal end further including an outlet port and a continuous passageway which communicates said suction aperture with said outlet port;

said reciprocation mechanism automatically reciprocating said hollow cannula relative to said hand-supportable housing along said longitudinal axis so that the location of aspiration through said suction aperture is periodically displaced along said longitudinal axis, while permitting aspiration through said suction aperture, along said continuous passageway, and out of said outlet port;

a radio-frequency (RF) power supply terminal disposed within said hand-holdable housing, for supplying to said hollow cannula, during liposuction operations, RF power signals produced by a RF power signal generator; and a cauterizing electrode provided about said suction aperture and electrically connected to said RF power supply terminal, for conducting said RF power signals about said suction aperture and through tissue being aspirated through said suction aperture while tissue is maintained at electrical ground potential by means of an electrical grounding plate connected to the patient, and thereby effecting coagulation of protein molecules within the tissue being aspirated through said suction aperture.

2. The apparatus of claim 1, wherein said hollow cannula further comprises a cannula base extending from said proximal end and being adapted for releasably connecting to said hand-holdable housing, and wherein said hollow cannula is operably associated with said reciprocation mechanism by way of an actuator disposed in said hand-holdable housing and reciprocatable by said reciprocation mechanism.

3. The apparatus of claim 1, wherein said hollow cannula is made from an electrically conductive material capable of conducting said RF power signals therealong to regions proximate said suction aperture during liposuction operations; and wherein said hollow cannula further comprises electrical insulation material applied over the outer surface of said hollow cannula.

4. The apparatus of claim 3, wherein said electrical isolation material comprises a coating of electrically insulating material applied to the outer surface of said hollow cannula.

5. The apparatus of claim 1, wherein said hollow cannula is electrically non-conductive, and wherein said hollow cannula further includes a cannula base having an electrical element for conducting said RF power signals from said RF power supply terminal to said cauterizing electrode.

6. The apparatus of claim 1, which further comprises said RF power signal generator.

7. A hand-supportable liposuction instrument for aspirating tissue on a patient operably connected to an electrical grounding plate, which comprises:

a hand-holdable housing having a longitudinal axis;

a reciprocation mechanism disposed within said hand-supportable housing;

a hollow cannula operably connectable to said hand-holdable housing and said reciprocation mechanism and having a distal end, a proximal end, and a suction aperture disposed about said distal end, said proximal end further including an outlet port and a continuous passageway which communicates said suction aperture with said outlet port;

said reciprocation mechanism automatically reciprocating said hollow cannula relative to said hand-supportable housing along said longitudinal axis so that the location of aspiration through said suction aperture is periodically displaced along said longitudinal axis, while permitting aspiration through said suction aperture, along said continuous passageway, and out of said outlet port;

a radio-frequency (RF) power supply terminal disposed within said hand-holdable housing, for supplying to said hollow cannula, during liposuction operations, RF power signals produced by a RF power signal generator; and a cauterizing electrode provided about said suction aperture and electrically connected to said RF power supply terminal, for conducting said RF power signals about said suction aperture and through tissue being aspirated through said suction aperture while tissue is maintained at electrical ground potential by means of an electrical grounding plate connected to the patient, and thereby effecting coagulation of protein molecules within the tissue being aspirated through said suction aperture.

8. The hand-supportable liposuction instrument of claim 7, which further comprises said RF power signal generator.

9. The hand-supportable liposuction instrument of claim 7, wherein said hollow cannula further comprises a cannula base extending from said proximal end and being adapted for releasably connecting to said hand-holdable housing, and wherein said hollow cannula is operably associated with said reciprocation mechanism by way of an actuator disposed in said hand-holdable housing and reciprocatable by said reciprocation mechanism.

10. The hand-supportable liposuction instrument of claim 7, wherein said hollow cannula is made from an electrically conductive material capable of conducting said RF power signals therealong to regions proximate said suction aperture during liposuction operations; and wherein said hollow cannula further comprises electrical insulation material applied over the outer surface of said hollow cannula.

11. The hand-supportable liposuction instrument of claim 10, wherein said electrical isolation material comprises a coating of electrically insulating material applied to the outer surface of said hollow cannula.

12. The hand-supportable liposuction instrument of claim 7, wherein said hollow cannula is electrically non-conductive, and wherein said hollow cannula further includes a cannula base having an electrical element for conducting said RF power signals from said RF power supply terminal to said cauterizing electrode.

* * * * *

UNITED STATES PATENT AND TRADEMARK OFFICE
CERTIFICATE OF CORRECTION

PATENT NO. : 6,394,973 B1
DATED : May 28, 2002
INVENTOR(S) : Robert L. Cucin

It is certified that error appears in the above-identified patent and that said Letters Patent is hereby corrected as shown below:

<u>Title page,</u>
Item [56], References Cited should include the following:
U.S. PATENT DOCUMENTS
-- 3,082,805 *    3/1963    Royce
   3,732,858 *    5/1973    Banko
   3,734,099 *    5/1973    Bender et al.
   3,945,375 *    3/1976    Banko
   3,955,579 *    5/1976    Bridgman
   3,994,297 *    11/1976    Kopf
   4,167,944 *    9/1979    Banko
   4,203,444 *    5/1980    Bonnell et al.
   4,311,140 *    1/1982    Bridgman
   4,314,560 *    2/1982    Helfgott et al.
   4,487,600 *    12/1984    Brownville et al.
   4,530,356 *    7/1985    Helfgott et al.
   4,536,180 *    8/1985    Johnson
   4,577,629 *    3/1986    Martinez
   4,589,414 *    5/1986    Yyoshida et al.
   4,735,605 *    4/1988    Swartz
   4,792,327 *    12/1988    Swartz
   4,815,462 *    3/1989    Clark
   4,850,354 *    7/1989    McGurk-Burleson et al.
   4,886,491 *    12/1989    Parisi et al.
   4,909,249 *    3/1990    Akkas et al.
   4,932,935 *    6/1990    Swartz
   4,940,468 *    7/1990    Petillo
   5,024,652 *    6/1991    Dumenek et al.
   5,106,364 *    4/1992    Hayafuji et al.
   5,186,714 *    2/1993    Boudreault et al.
   5,236,414 *    8/1993    Takasu
   5,277,696 *    1/1994    Hagen
   5,290,282 *    3/1994    Casscells
   5,364,395 *    11/1994    West, Jr.
   5,520,685 *    5/1996    Wojciechowicz
   5,643,198 *    6/1997    Cucin
   5,795,323 *    8/1998    Cucin
   5,797,907 *    8/1998    Clement
   6,102,885 *    8/2000    Bass --

UNITED STATES PATENT AND TRADEMARK OFFICE
CERTIFICATE OF CORRECTION

PATENT NO.    : 6,394,973 B1
DATED         : May 28, 2002
INVENTOR(S)   : Robert L. Cucin It is certified that error appears in the above-identified patent and that said Letters Patent is hereby corrected as shown below:

Item [56], References Cited, cont'd,
FOREIGN PATENT DOCUMENTS
-- 0 125 070 A2 11/1984 European Patent Office --

OTHER PUBLICATIONS
-- Body Contouring with Suction Lipectomy by Kesselring, Clinics in Plastic Surgery, Vol. 11, No. 3, 1984
Illouz s Technique of Body Contouring by Lipolysis by Illouz, Clinics in Plastic Surgery, Vol. 11, No. 3, 1984 --

Signed and Sealed this

Eleventh Day of February, 2003

JAMES E. ROGAN
*Director of the United States Patent and Trademark Office*